US012453553B2

(12) United States Patent
Schings et al.

(10) Patent No.: US 12,453,553 B2
(45) Date of Patent: Oct. 28, 2025

(54) OVERLAPPING STAPLE PATTERN FOR SURGICAL STAPLER

(71) Applicant: Cilag GmbH International, Zug (CH)

(72) Inventors: Brian D. Schings, Maineville, OH (US); Francesca N. Mayhaus, Independence, KY (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 17/485,589

(22) Filed: Sep. 27, 2021

(65) Prior Publication Data

US 2023/0107231 A1 Apr. 6, 2023

(51) Int. Cl.
*A61B 17/072* (2006.01)
*A61B 17/068* (2006.01)

(52) U.S. Cl.
CPC ........ *A61B 17/072* (2013.01); *A61B 17/0686* (2013.01); *A61B 2017/07264* (2013.01); *A61B 2017/07271* (2013.01)

(58) Field of Classification Search
CPC .............. A61B 17/072; A61B 17/0686; A61B 2017/07264; A61B 2017/07271
USPC ....................................................... 227/175.1
See application file for complete search history.

(56) References Cited

U.S. PATENT DOCUMENTS 2,277,931 A 3/1942 Moe
4,047,654 A 9/1977 Alvarado
4,407,286 A 10/1983 Noiles et al.
4,505,273 A 3/1985 Braun et al.
4,669,647 A 6/1987 Storace
4,848,328 A 7/1989 Laboureau et al.
4,874,122 A 10/1989 Froelich et al.
4,899,745 A 2/1990 Laboureau et al.
5,292,053 A 3/1994 Bilotti et al.
5,333,773 A 8/1994 Main et al.
(Continued)

FOREIGN PATENT DOCUMENTS

CN 202982106 U 6/2013
EP 0072754 A2 2/1983
(Continued)

OTHER PUBLICATIONS

International Search Report and Written Opinion dated Nov. 14, 2022, for International Application No. PCT/IB2022/057444, 12 pages.
(Continued)

*Primary Examiner* — Veronica Martin
(74) *Attorney, Agent, or Firm* — FROST BROWN TODD LLP

(57) ABSTRACT

A surgical stapling instrument includes an anvil and a stapling assembly. The stapling assembly includes first and second staples. The anvil is configured to deform the first and second staples to thereby transition the first and second staples from a non-deformed state to a deformed state. The first staple includes a first crown. The second staple includes a second crown and a first leg disposed at a first angle relative to the second crown in the non-deformed state. The first leg of the second staple is configured to extend over the first crown to form an overlapping staple pattern between the first and second staples when the first and second staples are in the deformed state.

20 Claims, 23 Drawing Sheets

(56) References Cited

U.S. PATENT DOCUMENTS 5,342,396 A 8/1994 Cook
5,350,104 A 9/1994 Main et al.
5,350,400 A 9/1994 Esposito et al.
5,389,098 A 2/1995 Tsuruta et al.
5,425,489 A 6/1995 Shichman et al.
5,484,451 A 1/1996 Akopov et al.
5,533,661 A 7/1996 Main et al.
5,571,285 A * 11/1996 Chow .................. A61B 17/105 606/75
5,725,554 A 3/1998 Simon et al.
5,732,872 A 3/1998 Bolduc et al.
5,833,695 A 11/1998 Yoon
6,352,541 B1 3/2002 Kienzle et al.
6,425,903 B1 7/2002 Voegele
6,616,686 B2 9/2003 Coleman et al.
6,767,356 B2 7/2004 Kanner et al.
6,915,937 B2 7/2005 Lat et al.
7,056,330 B2 6/2006 Gayton
7,404,508 B2 7/2008 Smith et al.
7,422,138 B2 9/2008 Bilotti et al.
7,434,715 B2 10/2008 Shelton, IV et al.
7,721,930 B2 5/2010 McKenna et al.
7,824,426 B2 11/2010 Racenet et al.
7,926,691 B2 4/2011 Viola et al.
8,143,870 B2 3/2012 Ng et al.
8,210,411 B2 7/2012 Yates et al.
8,328,063 B2 12/2012 Milliman et al.
8,408,439 B2 4/2013 Huang et al.
8,453,914 B2 6/2013 Laurent et al.
8,496,155 B2 7/2013 Knodel
8,590,762 B2 * 11/2013 Hess ..................... F02D 11/105 227/176.1
8,613,384 B2 12/2013 Pastorelli et al.
8,789,738 B2 7/2014 Knodel et al.
8,801,732 B2 8/2014 Harris et al.
8,910,847 B2 12/2014 Nalagatla et al.
9,016,541 B2 4/2015 Viola et al.
9,186,142 B2 11/2015 Fanelli et al.
9,192,387 B1 11/2015 Holsten et al.
9,265,500 B2 2/2016 Sorrentino et al.
9,402,628 B2 8/2016 Beardsley
9,517,065 B2 12/2016 Simms et al.
9,622,746 B2 4/2017 Simms et al.
9,713,469 B2 7/2017 Leimbach et al.
9,717,497 B2 8/2017 Zerkle et al.
9,782,171 B2 10/2017 Viola
9,795,379 B2 10/2017 Leimbach et al.
9,808,248 B2 11/2017 Hoffman
9,848,874 B2 12/2017 Kostrzewski
9,907,552 B2 3/2018 Measamer et al.
9,936,949 B2 4/2018 Measamer et al.
10,092,292 B2 10/2018 Boudreaux et al.
10,166,026 B2 1/2019 Shelton, IV et al.
10,265,073 B2 4/2019 Scheib et al.
10,285,705 B2 5/2019 Shelton, IV et al.
10,327,764 B2 6/2019 Harris et al.
10,463,368 B2 11/2019 Kostrzewski
10,639,040 B2 5/2020 Penna et al.
10,709,452 B2 7/2020 DiNardo et al.
10,898,187 B2 1/2021 Deck et al.
10,925,607 B2 2/2021 Penna et al.
11,033,266 B2 6/2021 Jones et al.
11,045,193 B2 6/2021 Schings et al.
11,241,232 B2 2/2022 Guerrera
11,284,890 B2 3/2022 Nalagatla et al.
11,432,815 B2 9/2022 Courtwright et al.
2002/0185517 A1 12/2002 Vresh et al.
2003/0078603 A1 4/2003 Schaller et al.
2004/0073237 A1 4/2004 Leinsing
2006/0291981 A1 12/2006 Viola et al.
2008/0082126 A1 4/2008 Murray et al.
2008/0210738 A1 9/2008 Shelton, IV et al.
2010/0191262 A1 7/2010 Harris et al.
2011/0011916 A1 1/2011 Levine
2012/0080339 A1* 4/2012 Shelton, IV ......... A61B 17/105 206/339
2012/0080498 A1 4/2012 Shelton, IV et al.
2012/0083836 A1 4/2012 Shelton, Iv et al.
2012/0241505 A1* 9/2012 Alexander, III ... A61B 17/1155 227/179.1
2013/0172929 A1 7/2013 Hess et al.
2014/0027493 A1 1/2014 Jankowski
2014/0081176 A1 3/2014 Hassan
2014/0158747 A1 6/2014 Measamer et al.
2014/0239037 A1 8/2014 Boudreaux et al.
2014/0263570 A1 9/2014 Hopkins et al.
2015/0083772 A1 3/2015 Miller et al.
2015/0297236 A1 10/2015 Harris et al.
2016/0270783 A1 9/2016 Yigit et al.
2016/0278768 A1 9/2016 Johnson et al.
2017/0119388 A1 5/2017 Kostrzewski
2017/0119397 A1 5/2017 Harris et al.
2017/0281187 A1 10/2017 Shelton, IV et al.
2018/0132849 A1 5/2018 Miller et al.
2018/0168599 A1 6/2018 Bakos et al.
2018/0168637 A1* 6/2018 Harris ................ A61B 17/0644
2018/0206844 A1 7/2018 Harris et al.
2018/0235613 A1* 8/2018 Shelton, IV ..... A61B 17/07292
2018/0235635 A1 8/2018 Rekstad et al.
2018/0242974 A1 8/2018 Guerrera et al.
2018/0325508 A1 11/2018 Aronhalt et al.
2019/0000481 A1* 1/2019 Harris ................ A61B 17/3468
2019/0008518 A1 1/2019 Sgroi, Jr. et al.
2019/0328390 A1 10/2019 Harris et al.
2020/0038017 A1 2/2020 Hess et al.
2020/0046353 A1 2/2020 Deck et al.
2020/0046355 A1 2/2020 Harris et al.
2020/0054338 A1 2/2020 Shen
2020/0054339 A1 2/2020 Scirica et al.
2020/0205835 A1 7/2020 Nalagatla et al.
2020/0229814 A1 7/2020 Amariglio et al.
2020/0246001 A1 8/2020 Ming et al.
2020/0281595 A1 9/2020 Wise et al.
2020/0337698 A1 10/2020 Simms
2021/0038223 A1 2/2021 Schings et al.
2021/0128150 A1 5/2021 Hopkins et al.
2021/0307749 A1 10/2021 Shelton, IV et al.
2023/0045940 A1 2/2023 Shelton, IV et al.
2023/0047471 A1 2/2023 Jones et al.
2023/0048389 A1 2/2023 Bruce et al.
2023/0049352 A1 2/2023 Shelton, IV et al.
2023/0051305 A1 2/2023 Jones et al.
2023/0053080 A1 2/2023 Jones et al.

FOREIGN PATENT DOCUMENTS

EP 1875870 A1 1/2008
EP 2157918 A1 3/2010
EP 2540231 A2 1/2013
EP 2649949 A1 10/2013
EP 3000407 A2 3/2016
EP 3225176 A1 10/2017
EP 3225179 A1 10/2017
EP 3245958 A1 11/2017
EP 3130292 B1 8/2018
EP 3173030 B1 10/2019
EP 3643252 A1 4/2020
RU 2066128 C1 9/1996
WO WO 1996/022055 A1 7/1996
WO WO 2001/054594 A1 8/2001
WO WO 2002/009595 A1 2/2002
WO WO 2005/115254 A2 12/2005
WO WO 2008/141288 A1 11/2008
WO WO 2020/249487 A1 12/2020
WO WO 2022/238841 A2 11/2022

OTHER PUBLICATIONS

International Search Report and Written Opinion dated Jan. 27, 2023, for International Application No. PCT/IB2022/057446, 19 pages.

(56) References Cited

OTHER PUBLICATIONS

International Search Report and Written Opinion dated Nov. 23, 2022, for International Application No. PCT/IB2022/057449, 15 pages.
International Search Report and Written Opinion dated Jan. 25, 2023, for International Application No. PCT/IB2022/057442, 20 pages.
International Search Report and Written Opinion dated Nov. 14, 2022, for International Application No. PCT/IB2022/057443, 12 pages.
International Search Report and Written Opinion dated Nov. 24, 2022, for International Application No. PCT/IB2022/057451, 13 pages.
U.S. Appl. No. 17/485,586, entitled "Staple and Staple-Forming Pocket Arrangements for Surgical Staplers," filed Sep. 27, 2021.
International Search Report and Written Opinion dated Dec. 19, 2022, for International Application No. PCT/IB2022/059020, 18 pages.
International Search Report and Written Opinion dated Dec. 14, 2022, for International Application No. PCT/IB2022/059023, 18 pages.
European Communication dated Feb. 26, 2025, for Application No. 22786478.2, 10 pages.

* cited by examiner

OVERLAPPING STAPLE PATTERN FOR SURGICAL STAPLER

BACKGROUND

Examples of surgical instruments include surgical staplers, which may be configured for use in laparoscopic surgical procedures and/or open surgical procedures. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein in its entirety.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
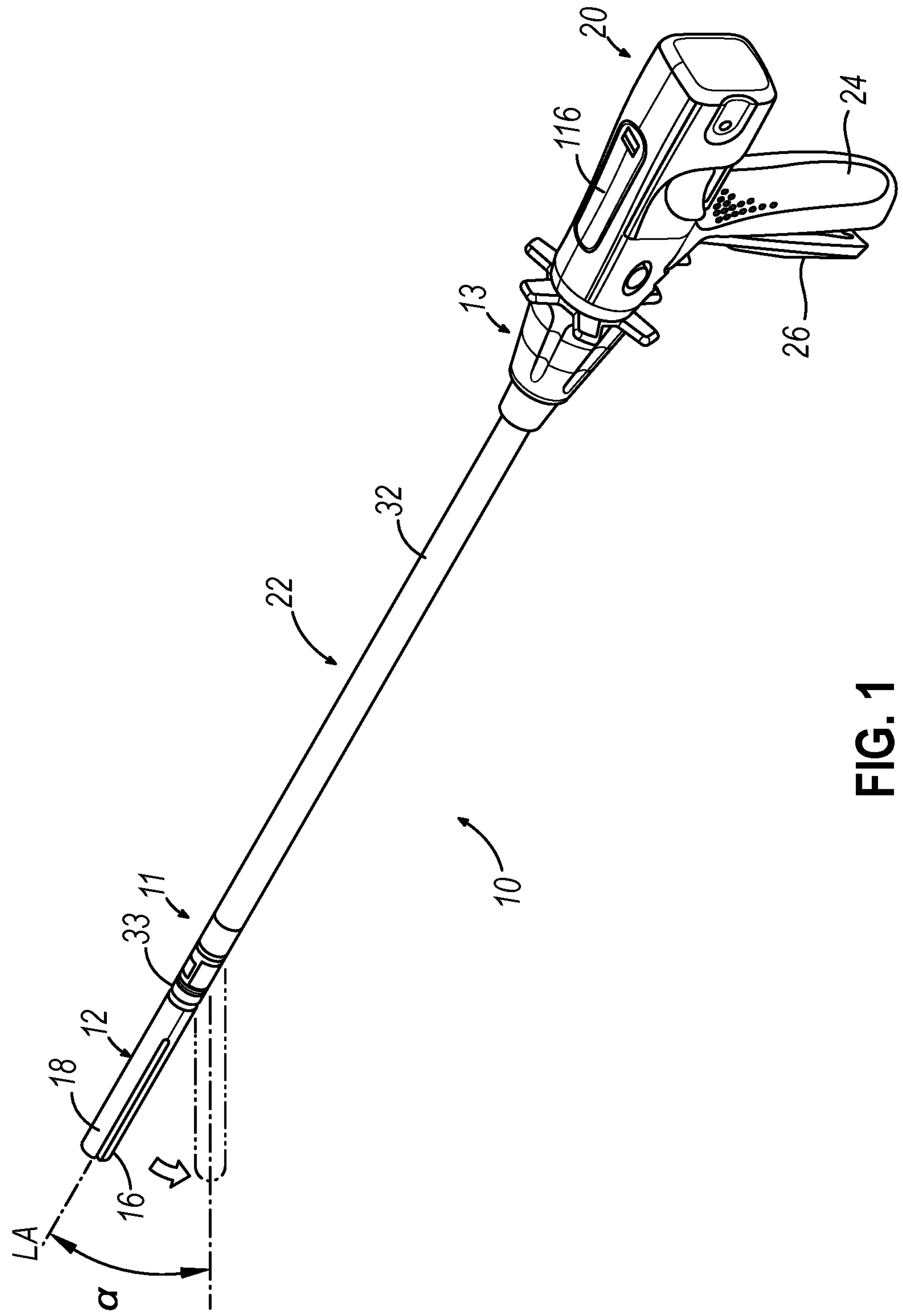
FIG. 1 depicts a perspective view of an example of an articulating surgical stapling instrument.
Figure 2:
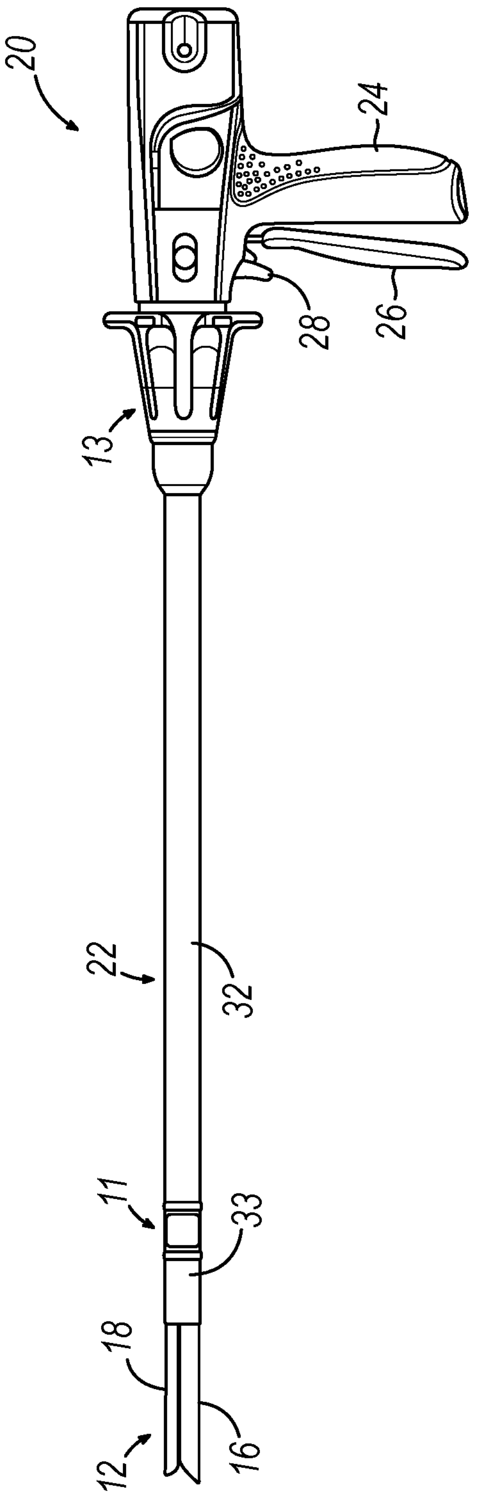
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

EXEMPLARY SURGICAL STAPLER

FIGS. 1-7 depict an example of a surgical stapling and severing instrument (10) that is sized for insertion, in a nonarticulated state as depicted in FIG. 1, through a trocar cannula, thoracotomy, or other incision to a surgical site in a patient for performing a surgical procedure. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20).

Once articulation joint (11) and end effector (12) are inserted into the patient, articulation joint (11) may be remotely articulated, as depicted in phantom in FIG. 1, by an articulation control (13), such that end effector (12) may be deflected from the longitudinal axis (LA) of shaft (22) at a desired angle (a). By way of example only, articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety; and/or U.S. Pat. No. 9,795,379, entitled "Surgical Instrument with Multi-Diameter Shaft," issued Oct. 24, 2017, the disclosure of which is incorporated by reference herein in its entirety. Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). By way of example only, lower jaw (16) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (18) may be constructed and operable in accordance with at least some of the teachings of at least some of the teachings of U.S. Pat. No. 10,092,292, entitled "Staple Forming Features for Surgical Stapling Instrument," issued Oct. 9, 2018, the disclosure of which is incorporated by reference herein in its entirety. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of tissue clamped in end effector (12), as will be described in greater detail below. Thereafter, triggers (26, 28) may be released to release the tissue from end effector (12).

Figure 4A:
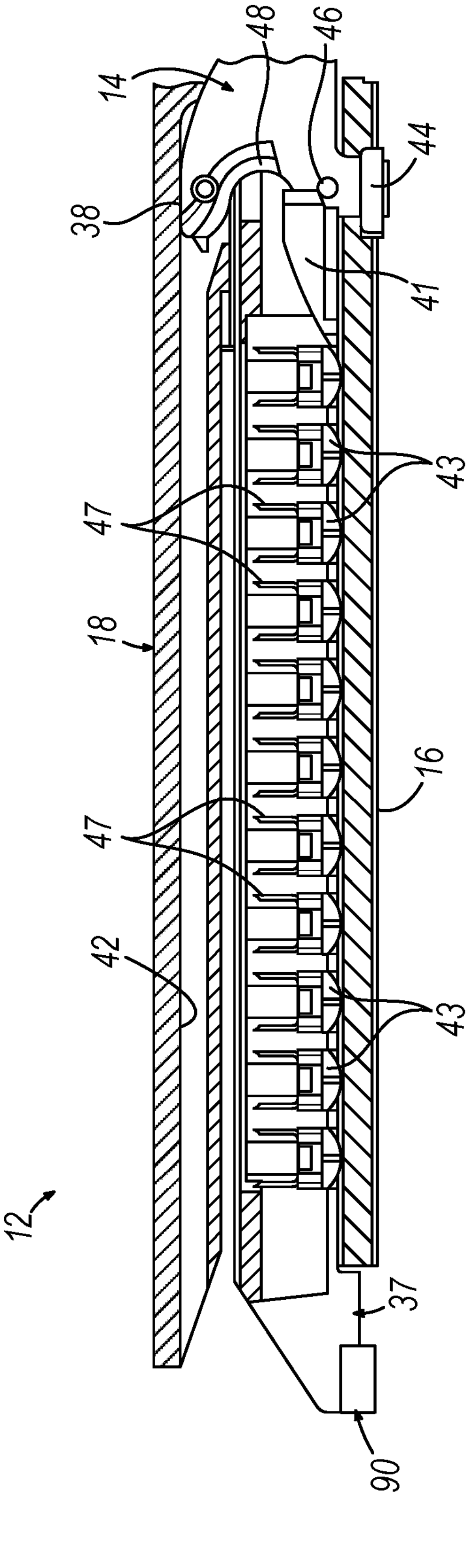
FIG. 4A depicts a side cross-sectional view of the end effector of FIG. 3, taken along line 4-4 of FIG. 3, with a firing beam in a proximal position.
Figure 4B:
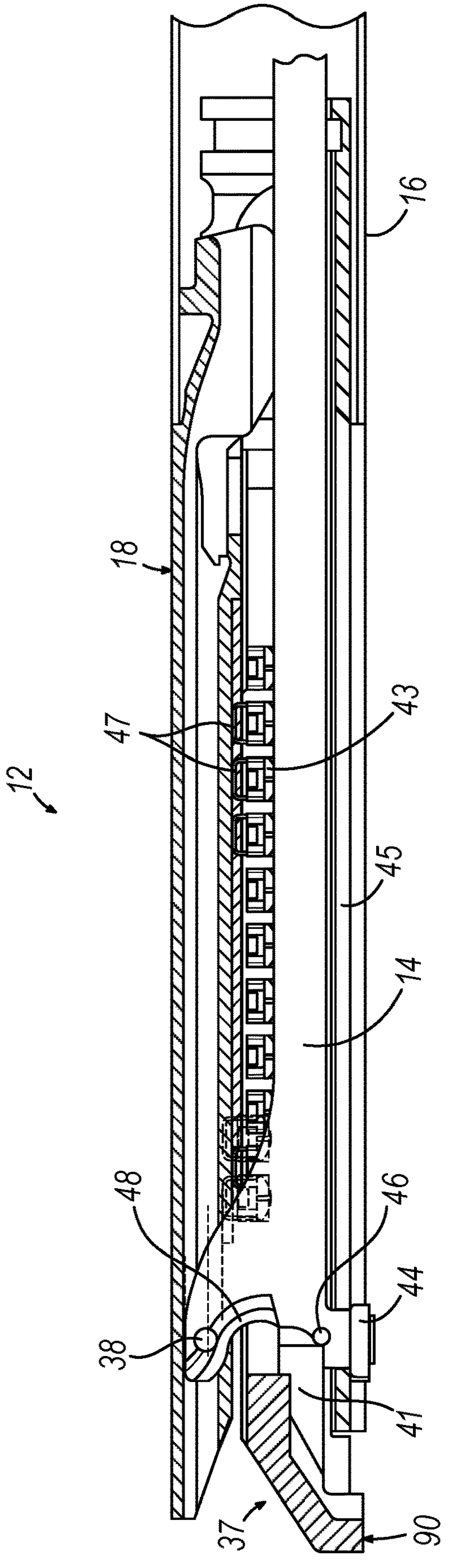
FIG. 4B depicts a side cross-sectional view of the end effector of FIG. 3, taken along line 4-4 of FIG. 3, with the firing beam in a distal position.

As best seen in FIGS. 4A-4B, firing beam (14) of the present example includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein in its entirety. Other suitable forms that firing beam (14) may take will be apparent to those skilled in the art in view of the teachings herein.

Figure 3:
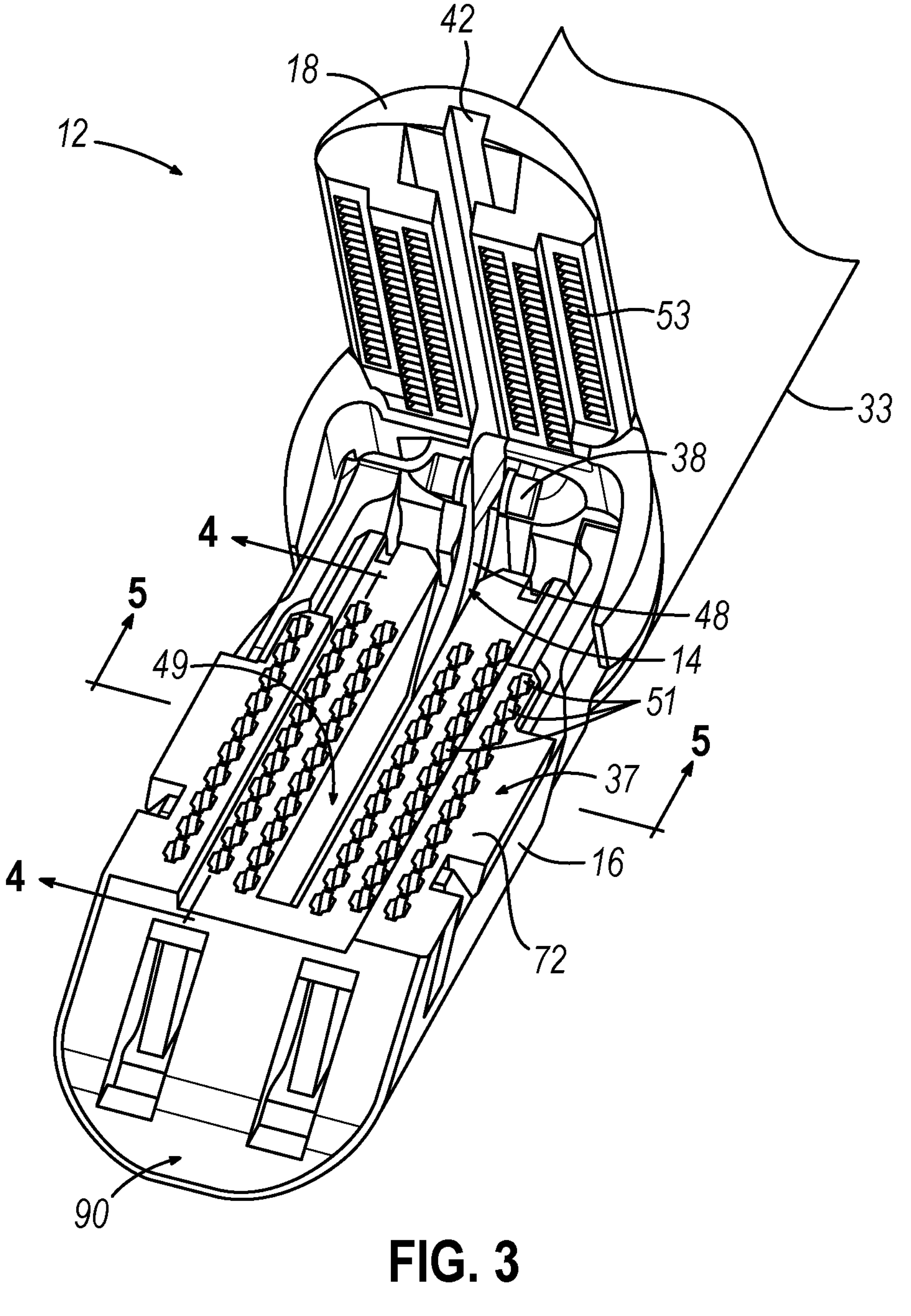
FIG. 3 depicts a perspective view of an opened end effector of the instrument of FIG. 1.
Figure 5:
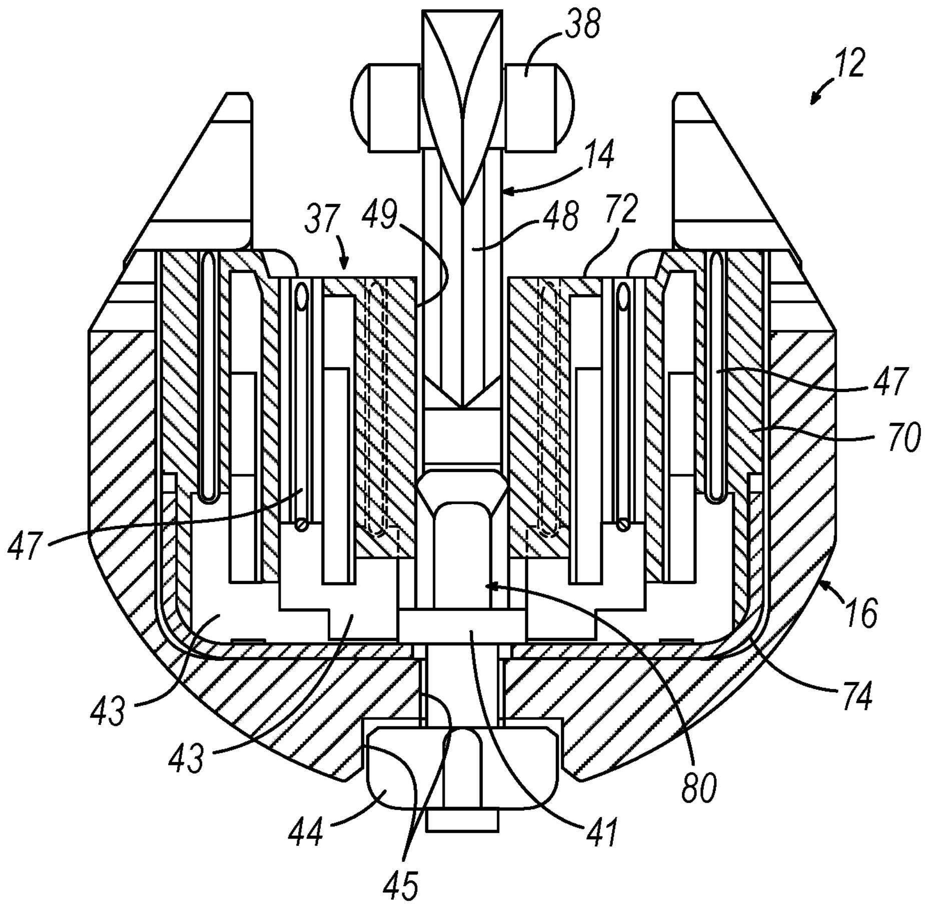
FIG. 5 depicts an end cross-sectional view of the end effector of FIG. 3, taken along line 5-5 of FIG. 3.
Figure 6:
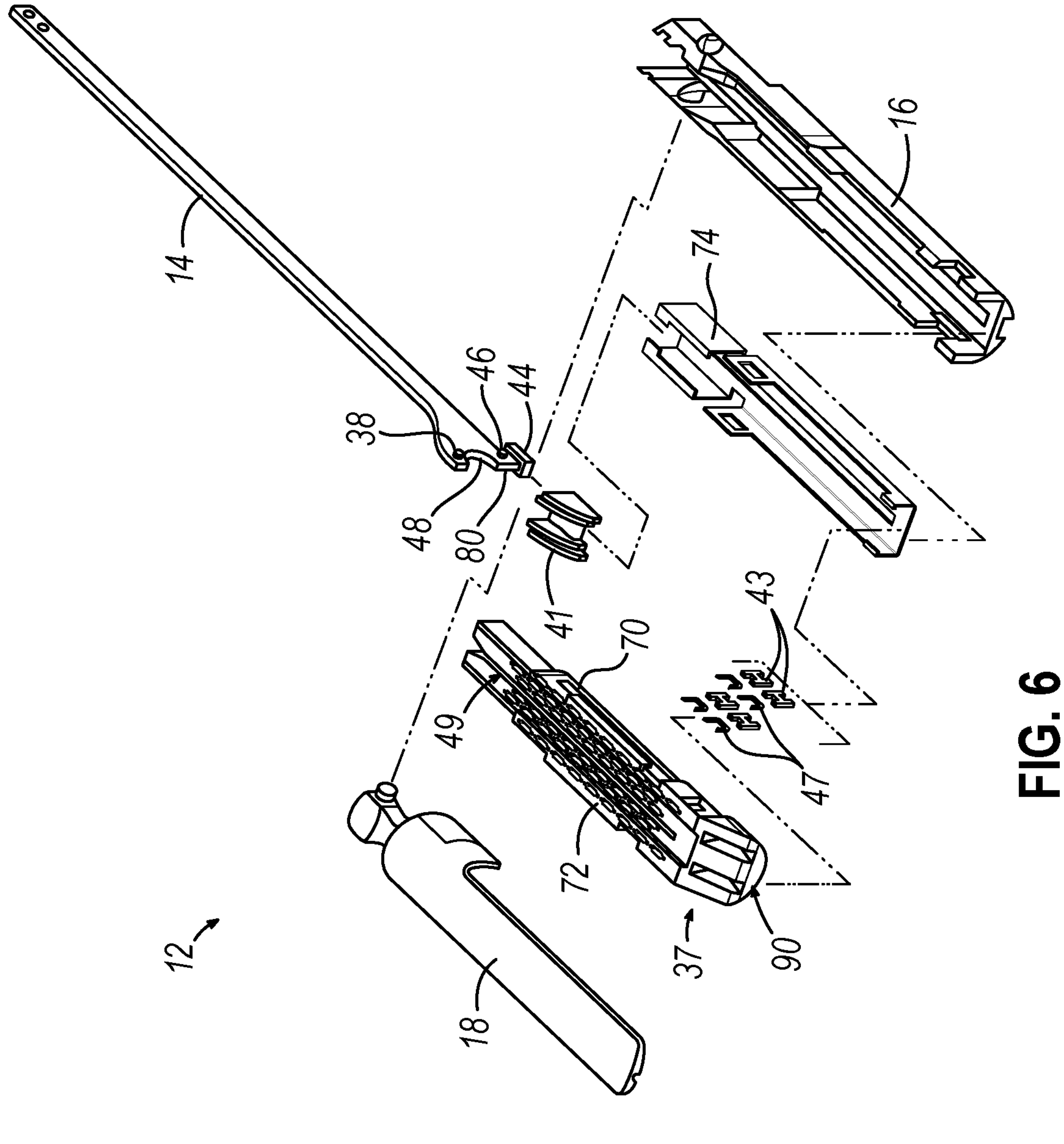
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). Three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43) when staple cartridge (37) is in a pre-fired (or "unspent") state. Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

By way of example only, staple cartridge (37) may be constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein in its entirety. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) located at the distal end of firing beam (14) is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
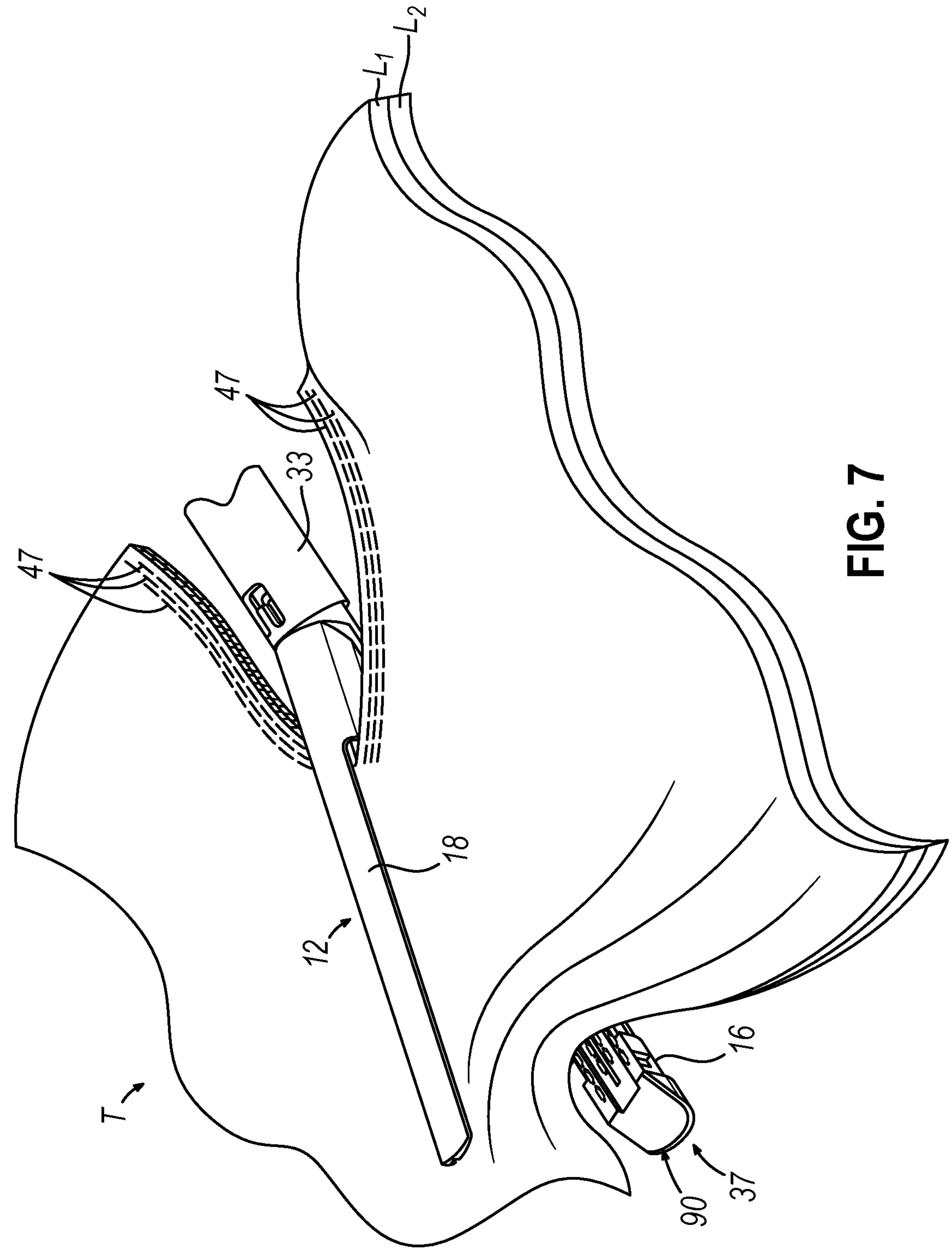
FIG. 7 depicts a perspective view of the end effector of FIG. 3, positioned at tissue and having been actuated once in the tissue.

FIG. 7 shows end effector (12) having been actuated through a single stroke through layers ($L_1$, $L_2$) of tissue (T). As shown, cutting edge (48) (obscured in FIG. 7) has cut through tissue (T), while staple drivers (43) have driven three alternating rows of staples (47) through the tissue (T) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar or incision after the first stroke is complete, spent staple cartridge (37) is replaced with a new staple cartridge, and end effector (12) is then again inserted through the trocar or incision to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

In some versions, instrument (10) provides motorized control of firing beam (14). By way of example only, such motorization may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein in its entirety; and/or U.S. Pat. No. 8,210,411, entitled "Motor-Driven Surgical Instrument," issued Jul. 3, 2012, the disclosure of which is incorporated by reference herein in its entirety. Other suitable components, features, and configurations for providing motorization of firing beam (14) will be apparent to those skilled in the art in view of the teachings herein. It should also be understood that some other versions may provide manual driving of firing beam (14), such that a motor may be omitted.

EXEMPLARY STAPLES AND EXEMPLARY ANVILS

It may be desirable to modify staples (47) of staple cartridge (37) and/or anvil (18) described above to increase staple density. As used herein, staple density is intended to refer to the number of staples per unit area of the staple cartridge. Higher staple density may provide increased seal strength against luminal leakage through the formed staple pattern. It is also beneficial to reduce time and associated costs of manufacturing, inspecting, and qualifying anvil (18) for use with instrument (10) of FIG. 1. It may also be beneficial to reduce the dimensions of anvil (18) while still providing adequate stapling functionality so that instrument (10) may more easily access the desired anatomy of the patent.

As will be described below with reference to FIGS. 8A-18, exemplary staples (110, 112, 210, 212, 214, 216, 276, 278, 280, 282) may be used instead of staples (47, 310) of staple cartridge (37). Staples (110, 112, 210, 212, 214, 216, 276, 278, 280, 282) may be incorporated into a stapling assembly, which may include features similar to staple cartridge (37) shown and described above with reference to FIGS. 3-7. Portions (e.g., legs) of staples (110, 112, 210, 212, 214, 216, 276, 278, 280, 282, 710) may overlap adjacent staples to form an overlapping staple pattern to increase robustness and strength of the staple line as a whole and which may allow for increased staple density. Staples (110, 112, 210, 212, 214, 216, 276, 278, 280, 282) may be used in conjunction with first and second exemplary alternative anvils (218, 410, 510), and staples (710) may be used in conjunction with a third exemplary alternative anvil (610). Anvils (218, 410, 510, 610) may require reduced time and associated costs of manufacturing, inspecting, and qualifying anvils (218, 410, 510, 610).

A. First Exemplary Alternative Staples

FIGS. 8-11 show schematic views of first exemplary alternative staples, shown as first and second staples (110, 112), which may be incorporated into the instrument (10) of FIG. 1. While first and second staples (110, 112) are shown, the principles pertaining to first and second staples (110, 112) also apply to additional staples (e.g., a third staple, a fourth staple, a fifth staple, and a sixth staple, etc.).

First staple (110) may exit a first staple aperture (114) of a deck surface (116), which may be generally similar to staple aperture (51) of upper deck (72) shown in FIG. 3. Similarly, second staple (112) may exit a second staple aperture (118) of deck surface (116) similar to first staple aperture (114). First and second staples (110, 112) are configured to transition from a non-deformed state shown in FIGS. 8A and 9A to a deformed state shown in FIGS. 8B and 9B-11 using an anvil (not shown but which may be similar to anvil (18)) when end effector (12) is in the closed configuration of FIG. 4A. First staple (110) is separate and discrete from second staple (112). First staple (110) includes a first crown (120) and a plurality of legs, shown as first and second legs (122, 124). First leg (122) extends from a first end (126) of first crown (120). Similarly, second leg (124) extends from a second end (128) of first crown (120) that is disposed opposite first end (126). First leg (122) includes a first terminal end (130), and second leg (124) includes a second terminal end (132). First and second terminal ends (130, 132) are shown as being sharp and pointed. As shown, first and second legs (122, 124) are generally straight in the non-deformed state. While first and second angles (β1, β2) of first and second legs (122, 124) relative to first crown (120) are shown as being generally equal, first and second angles (β1, β2) may be different.

Similar to first staple (110), second staple (112) includes a second crown (134) and a plurality of legs, which are shown as first and second legs (136, 138). First leg (136) extends from a first end (140) of second crown (134). Similarly, second leg (138) extends from a second end (142) of second crown (134) that is opposite first end (140). First leg (136) includes a first terminal end (144), and second leg (138) includes a second terminal end (146). First and second terminal ends (144, 146) are shown as being sharp and pointed. As shown, first and second legs (136, 138) are generally straight in the non-deformed state.

Figure 8A:
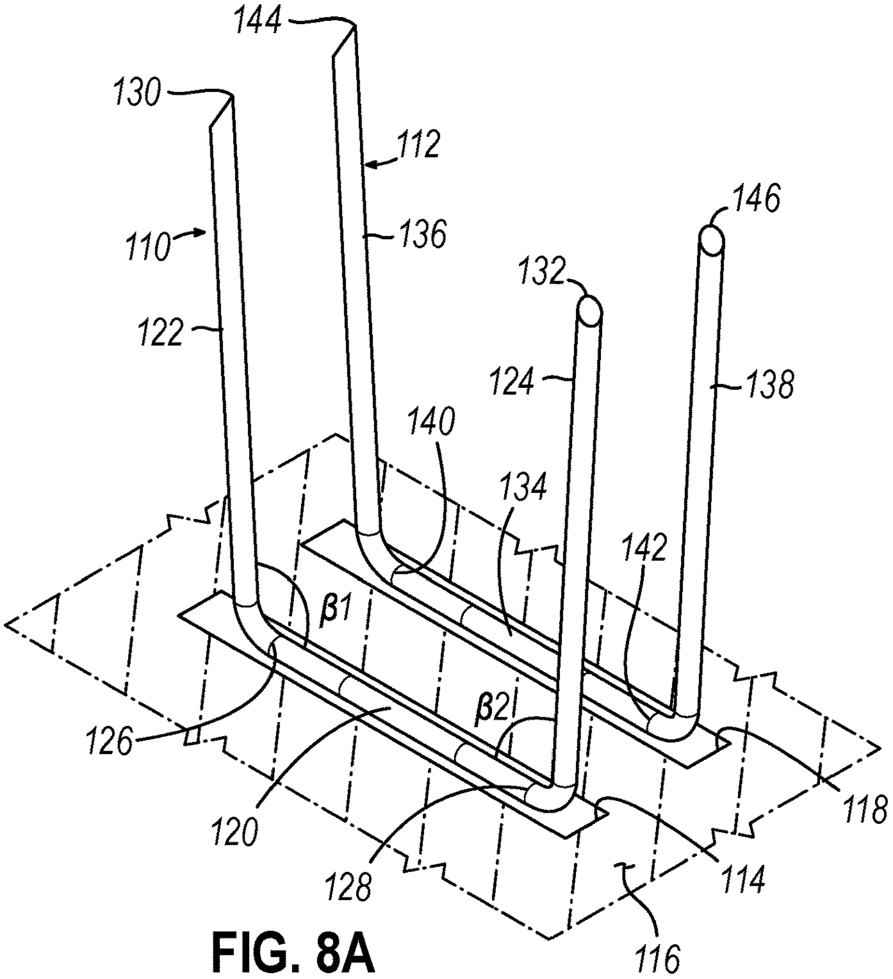
FIG. 8A depicts a schematic perspective view of first exemplary alternative staples in a non-deformed state, which may be incorporated into the instrument of FIG. 1.
Figure 8B:
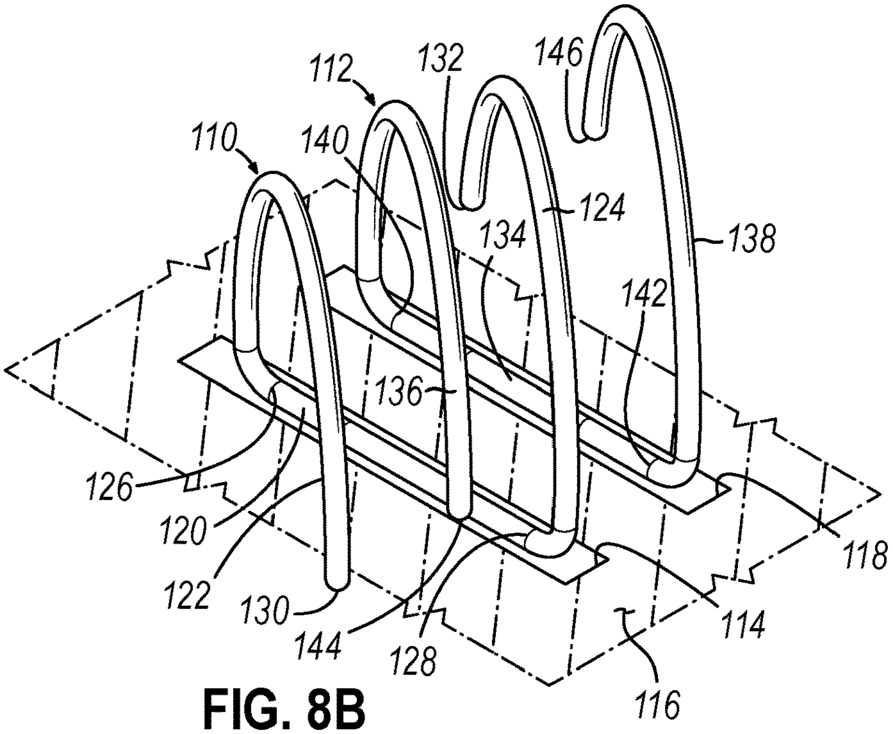
FIG. 8B depicts a schematic perspective view of the staples of FIG. 8A in a deformed state where portions of the staples overlap one another.
Figure 9A:
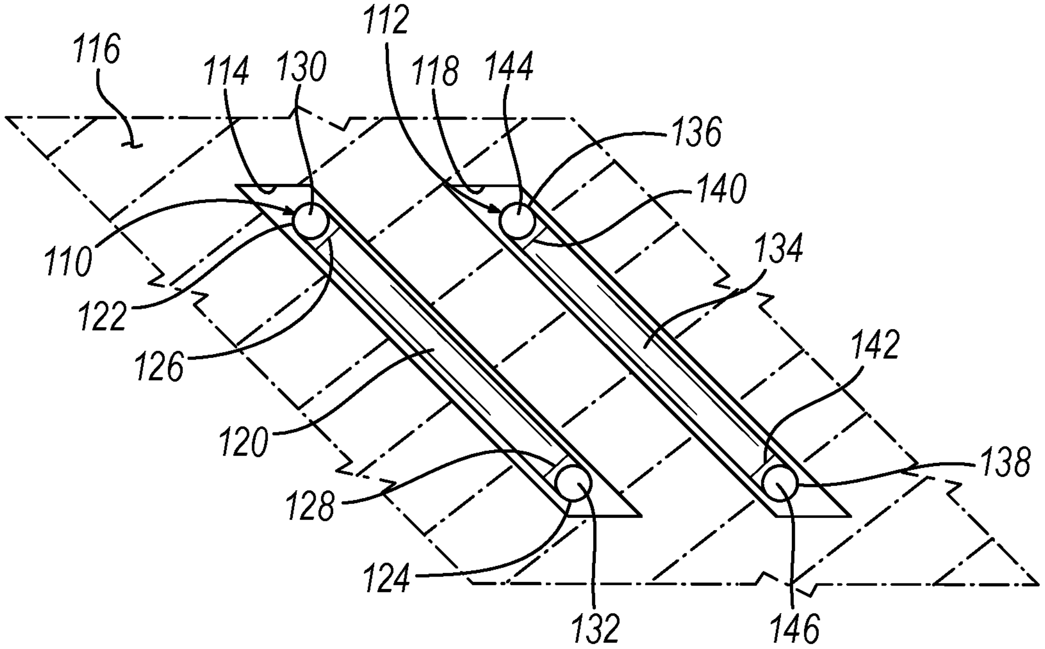
FIG. 9A depicts a schematic top view of the staples of FIG. 8A.
Figure 9B:
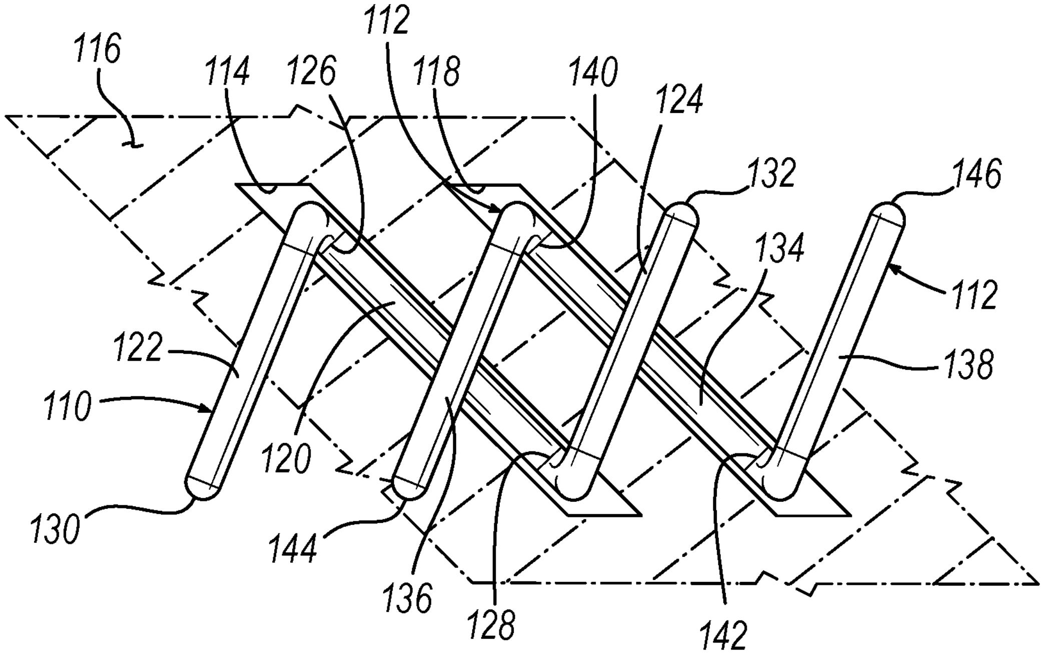
FIG. 9B depicts a schematic top view of the staples of FIG. 8B.

When first staple (110) is transitioned from the non-deformed state of FIGS. 8A and 9A to the deformed state of FIGS. 8B and 9B-11, second leg (124) of first staple (110) is configured to extend over second crown (134) to form an overlapping staple pattern between first and second staples (110, 112). Additionally, when first staple (110) is transitioned from the non-deformed state to the deformed state, first leg (122) of first staple (110) is configured to extend over a crown of another staple (not shown but which may be similar to first and second staples (110, 112)) to form an overlapping staple pattern. Similar to first staple (110), when second staple (112) is transitioned from the non-deformed state to the deformed state, first leg (136) of second staple (112) is configured to extend over first crown (120) of first staple (110) to form an overlapping staple pattern between first and second staples (110, 112). Second leg (138) of second staple (112) is configured to extend over third crown of a third staple (not shown) to form an overlapping staple pattern between second staple (112) and the third staple (not shown) when transitioned to the deformed state. The overlap of first and second staples (110, 112) may increase robustness and strength of the staple line as a whole and may allow for increased staple density.

Figure 10:
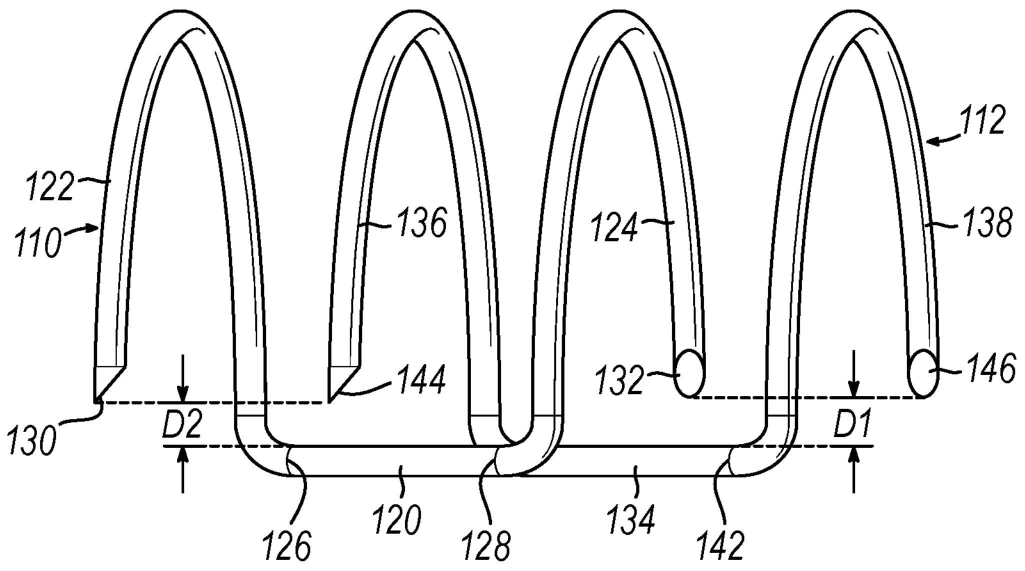
FIG. 10 depicts a schematic side elevational view of the staples of FIG. 8B.
Figure 11:
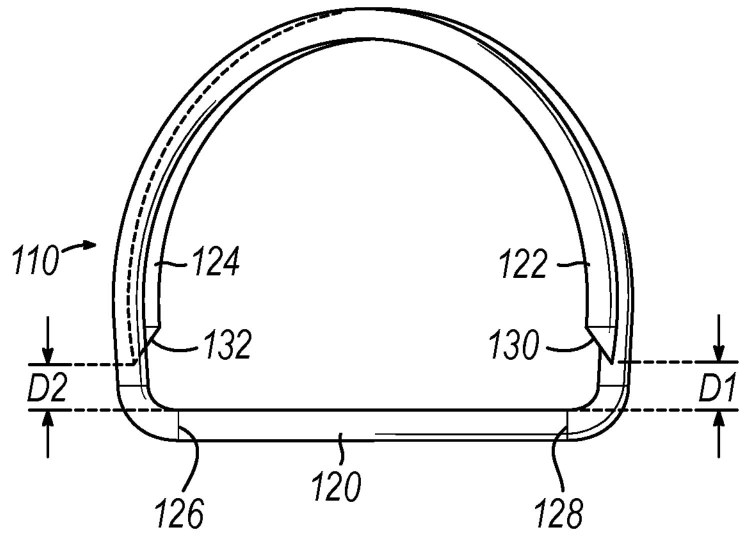
FIG. 11 depicts a schematic end view of the staples of FIG. 8B.

In the deformed state shown in FIGS. 8B, 10, and 11, first legs (122, 136) and second legs (124, 138) may be bent arcuately. In other words, in the deformed state, first and second legs (122, 124, 136, 138) of first and second staples (110, 112) each form a semicircle that terminates at first and second distances (D1, D2) away from an upper surface of first and second crowns (120, 134). As shown in the deformed state of FIG. 9B, first legs (122, 136) of first and second staples (110, 112) extend generally parallel to one another. Similarly, second legs (124, 138) of first and second staples (110, 112) extend generally parallel to one another and approximately 180 degrees opposite first legs (122, 136). While first and second staples (110, 112) are not shown as being in direct contact with each other, first and second staples (110, 112) appear interleaved together. While first and second distances (D1, D2) are shown as being equal, first and second distances (D1, D2) may be different. Staple drivers (not shown), but which may be similar to staple drivers (43), are configured to contact first and second crowns (120, 134) and drive first and second crowns (120, 134) toward the anvil (e.g., anvil (18)). First and second crowns (120, 134) may extend parallel to one another in each of the non-deformed and deformed states. As shown, second crown (134) is parallel to and offset from first crown (120) by a fixed distance. The fixed distance is the same for the non-deformed and deformed states. Each of first and second staples (110, 112) may be configured to contact a recessed surface of a staple forming pocket of an anvil (e.g., anvils (218, 410, 510) described below) to transition from the non-deformed state to the deformed state.

B. Second Exemplary Alternative Staples and First Exemplary Alternative Anvil

FIGS. 12-18 show schematic views of second exemplary alternative staples, shown as first, second, third, and fourth staples (210, 212, 214, 216), which may be incorporated into the instrument of FIG. 1. While first, second, third, and fourth staples (210, 212, 214, 216) are shown, the principles also apply to additional staples (e.g., a fifth staple, a sixth staple, a seventh staple, an eighth staple, a ninth staple, etc.). First, second, third, and fourth staples (210, 212, 214, 216) are configured to transition from a non-deformed state shown in FIGS. 12A, 13A, 14A, and 15A to a deformed state shown in FIGS. 12B, 13B, 14B, 15C-18 using anvil (218). First, second, third, and fourth staples (210, 212, 214, 216) are separate and discrete from one another.

First staple (210) includes a first crown (220) and a plurality of legs, shown as first and second legs (222, 224). First leg (222) extends from a first end (226) of first crown (220). Similarly, second leg (224) extends from a second end (228) of first crown (220) that is disposed opposite first end (226). First leg (222) includes a first terminal end (230), and second leg (224) includes a second terminal end (232). Similar to first staple (210), second staple (212) includes a second crown (234) and a plurality of legs, which are shown as first and second legs (236, 238). First leg (236) extends from a first end (240) of second crown (234). Similarly, second leg (238) extends from a second end (242) of second crown (234) that is opposite first end (240). First leg (236) includes a first terminal end (244), and second leg (238) includes a second terminal end (246). Similar to first and second staples (210, 212), third staple (214) includes a third crown (248) and a plurality of legs, which are shown as first and second legs (250, 252). First leg (250) extends from a first end (254) of third crown (248). Similarly, second leg (252) extends from a second end (256) of third crown (248) that is opposite first end (254). First leg (250) includes a first terminal end (258), and second leg (252) includes a second terminal end (260).

Similar to first, second, and third staples (210, 212, 214), fourth staple (216) includes a fourth crown (262) and a plurality of legs, which are shown as first and second legs (264, 266). First leg (264) extends from a first end (268) of fourth crown (262). Similarly, second leg (266) extends from a second end (270) of fourth crown (262) that is opposite first end (268). First leg (250) includes a first terminal end (272), and second leg (266) includes a second terminal end (274). First and second terminal ends (230, 232, 244, 246, 258, 260, 272, 274) are shown as being sharp and pointed. As shown in the non-deformed state, first and second legs (222, 224, 236, 238, 250, 252, 264, 266) are generally straight. In the non-deformed state, first leg (236) of second staple (212) is spaced a distance from first crown (220), While first angle (β3) of first leg (222, 236, 250, 264) is shown as being generally equal to second angle (β4) of second leg (224, 238, 252, 266), first and second angles (β3, β4) may be different. Each of first, second, third, and fourth staples (210, 212, 214, 216) may be configured to contact a staple forming pocket (219) of anvil (218) to transition from the non-deformed state to the deformed state. Unlike anvil (18) where each staple (47) has a corresponding staple forming pocket (53), second, third, and fourth staples (210, 212, 214, 216), anvil (218) may be configured to contact the same staple forming pocket (219).

When first staple (210) is transitioned from the non-deformed state to the deformed state, second leg (224) of first staple (210) is configured to extend over second crown (234) to form an overlapping staple pattern between first and second staples (210, 212). Additionally, when first staple (210) is transitioned from the non-deformed state to the deformed state, first leg (222) of first staple (210) is configured to extend over a crown of another staple (not shown), but which may be similar to first, second, third, and fourth staples (210, 212, 214, 216) to form an overlapping staple pattern. Similar to first staple (210), when second staple (212) is transitioned from the non-deformed state to the deformed state, first leg (236) of second staple (212) is configured to extend over first crown (220) of first staple (210) to form an overlapping staple pattern between first and second staples (210, 212). Second leg (238) of second staple (212) is configured to extend over third crown (248) of third staple (214) to form an overlapping staple pattern between second and third staples (212, 214) when transitioned to the deformed state. In the deformed state, first leg (236) is configured to occupy a space between first crown (220) and anvil (218).

Similar to second staple (212), when third staple (214) is transitioned from the non-deformed state to the deformed state, first leg (250) of third staple (214) is configured to extend over second crown (234) of second staple (212) to form an overlapping staple pattern between second and third staples (212, 214). Second leg (252) of third staple (212) is configured to extend over fourth crown (262) of fourth staple (216) to form an overlapping staple pattern between third and fourth staples (214, 216) when transitioned to the deformed state. Similar to third staple (214), when fourth staple (216) is transitioned from the non-deformed state to the deformed state, first leg (264) of fourth staple (216) is configured to extend over third crown (248) of third staple (214) to form an overlapping staple pattern between third and fourth staples (214, 216).

Figure 12A:
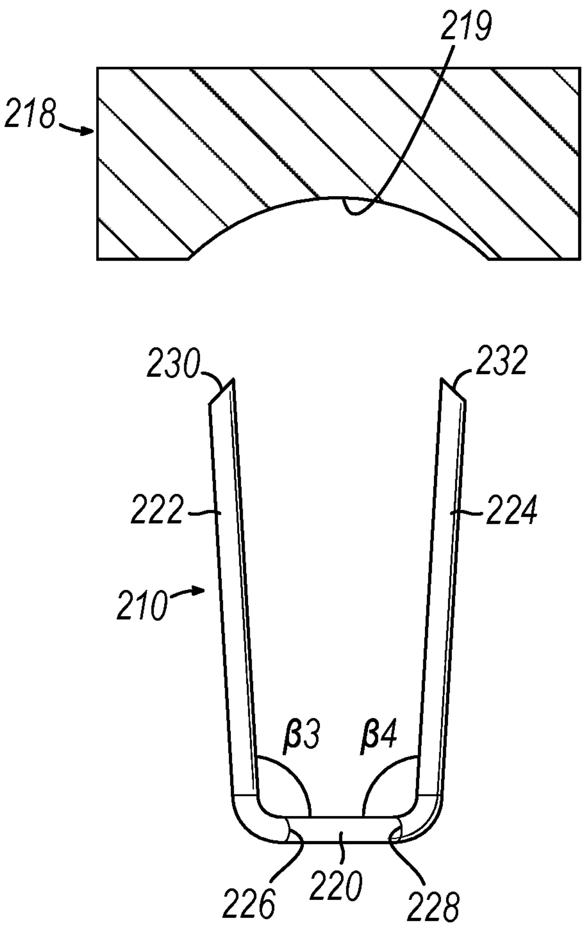
FIG. 12A depicts an end view of second exemplary alternative staples in a non-deformed state spaced from a first exemplary alternative anvil, shown in cross-section, which may be incorporated into the instrument of FIG. 1.
Figure 12B:
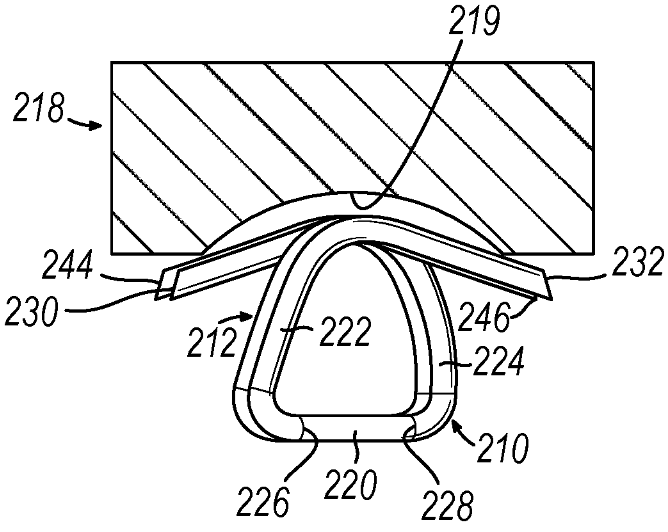
FIG. 12B depicts an end view of the staples of FIG. 12A in a deformed state against the anvil of FIG. 12A where portions of the staples overlap one another.
Figure 13A:
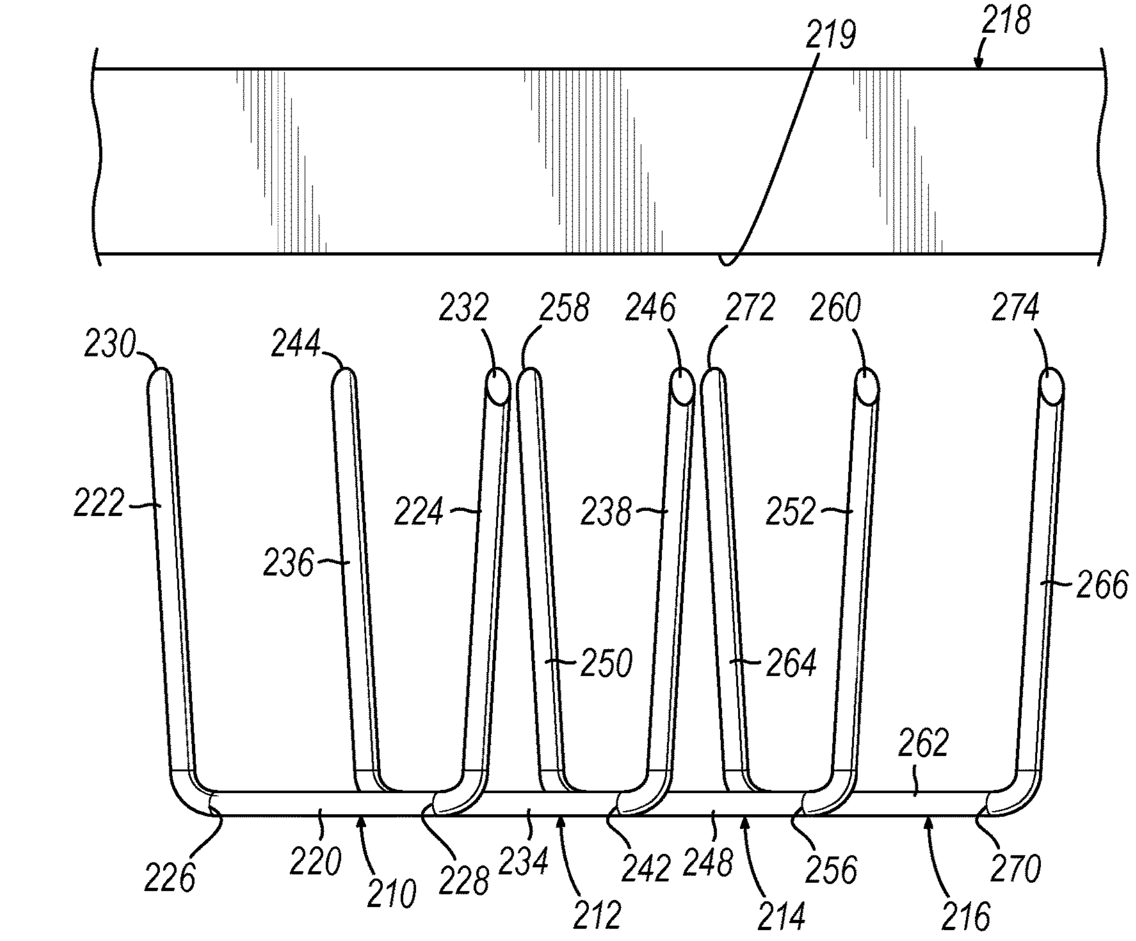
FIG. 13A depicts a side elevational view of the staples and the anvil of FIG. 12A.
Figure 13B:
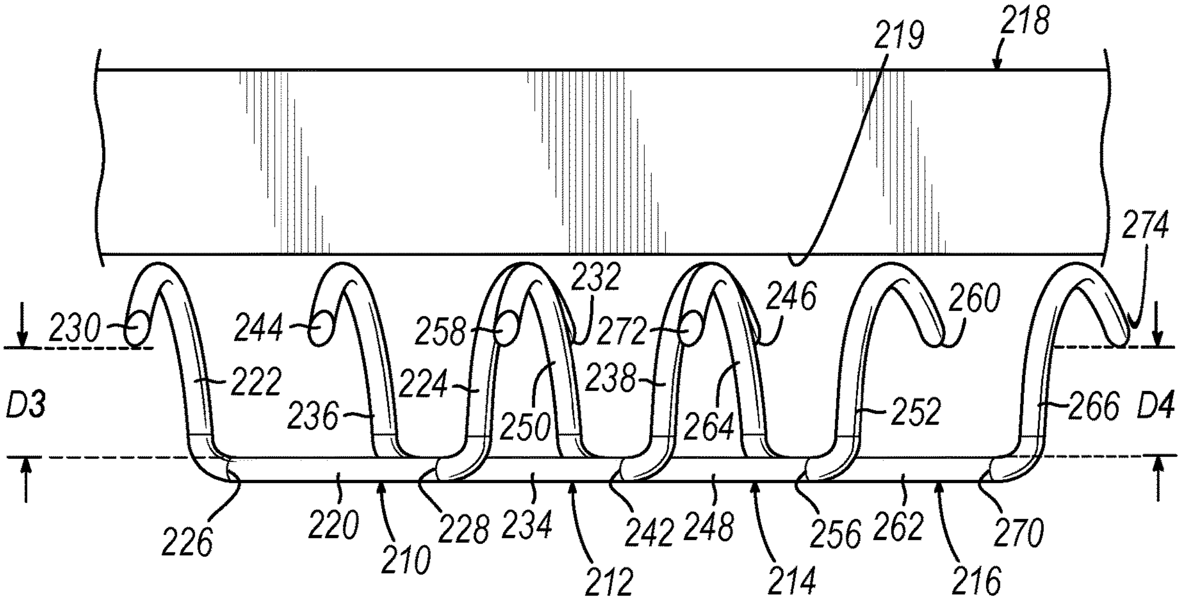
FIG. 13B depicts a side elevational view of the staples and the anvil of FIG. 12B.
Figure 14A:
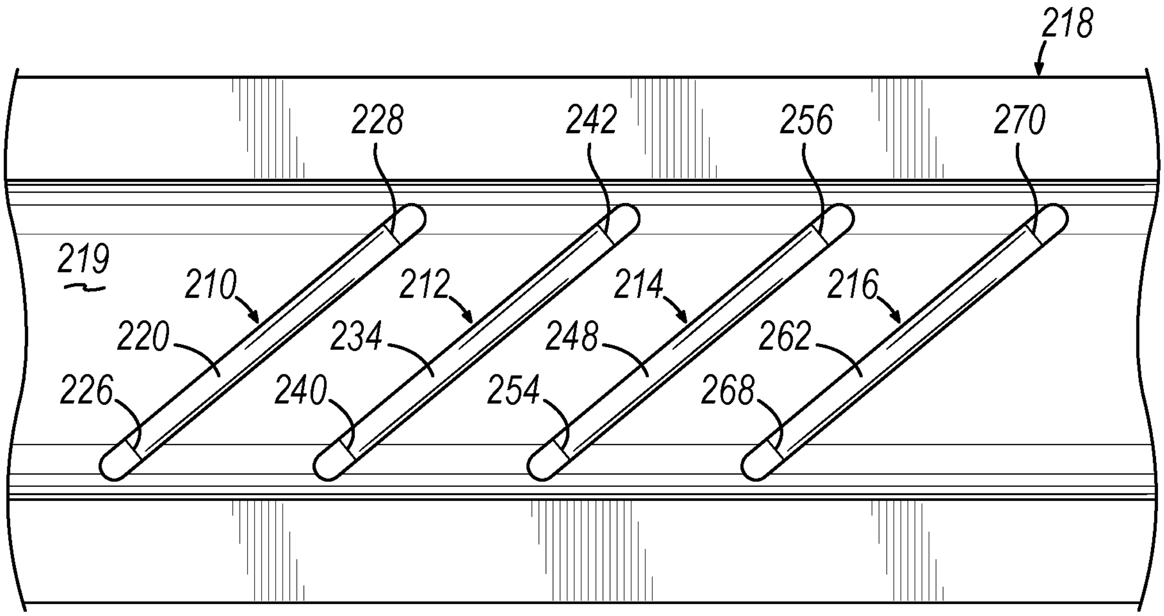
FIG. 14A depicts a bottom view of the staples and the anvil of FIG. 12A.
Figure 14B:
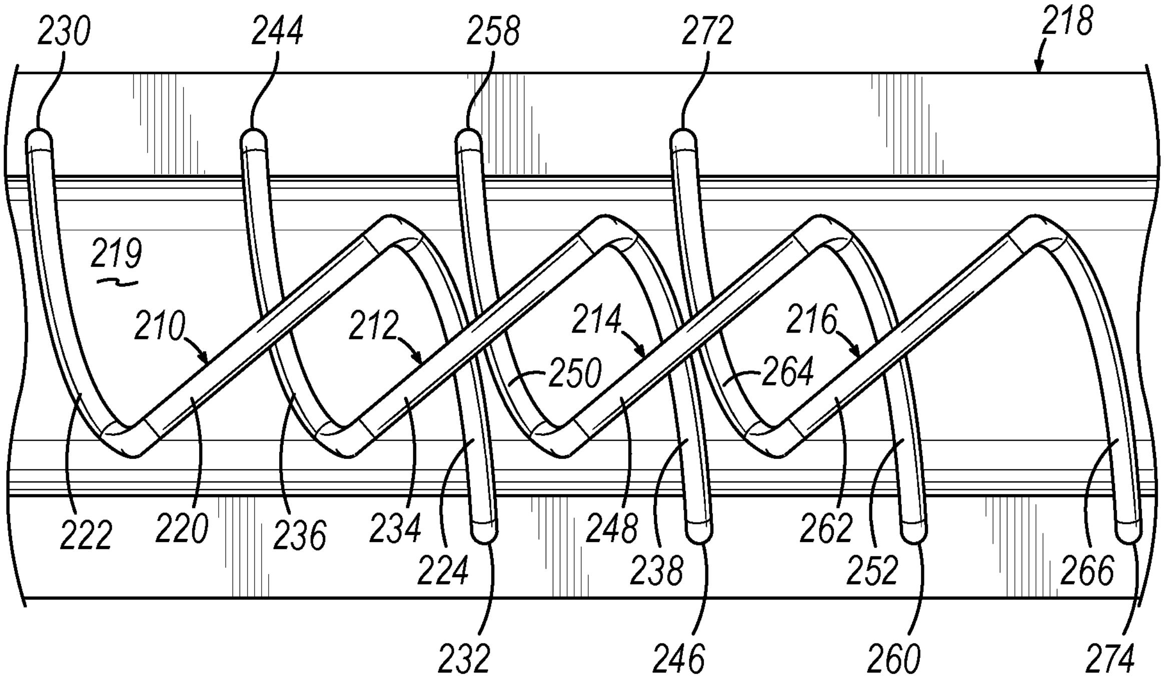
FIG. 14B depicts a bottom view of the staples and the anvil of FIG. 12B.
Figure 15A:
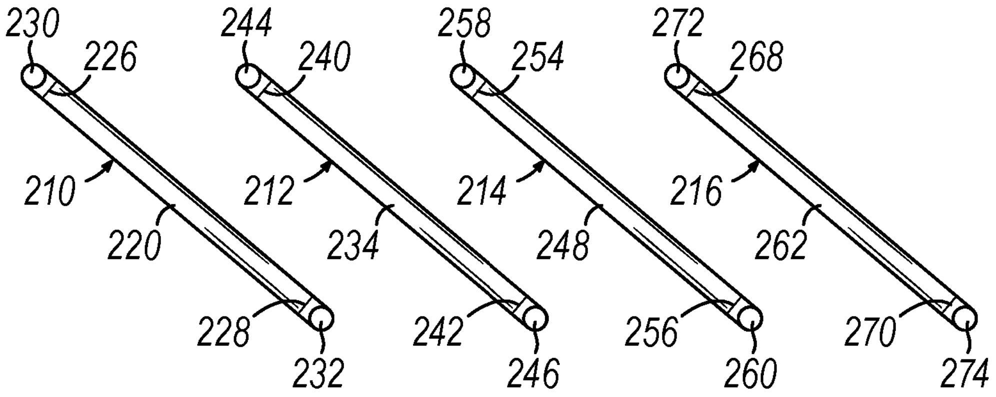
FIG. 15A depicts a top view of the staples of FIG. 12A.
Figure 15B:
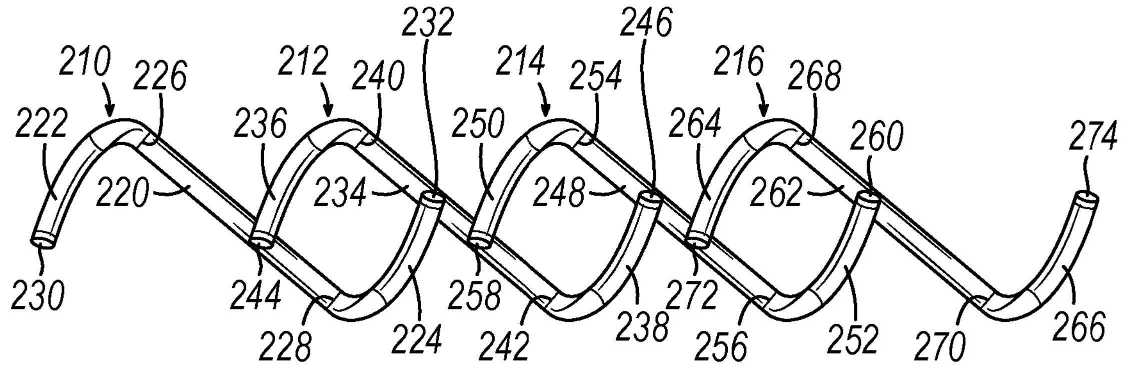
FIG. 15B depicts a top view of the staples of FIG. 15A, but in a partially deformed state.
Figure 15C:
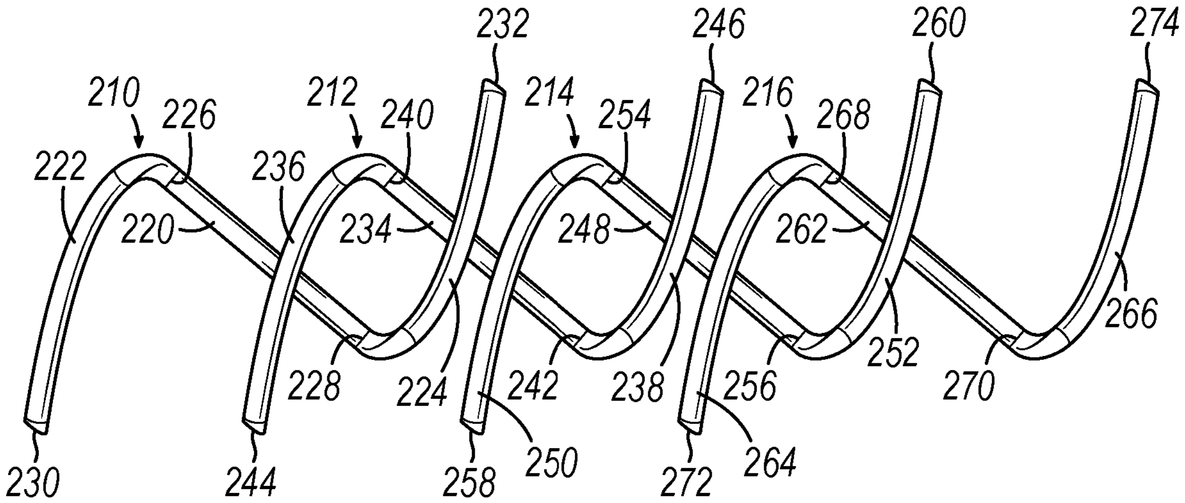
FIG. 15C depicts a top view of the staples of FIG. 15B, but in the deformed state of FIG. 12B.
Figure 16:
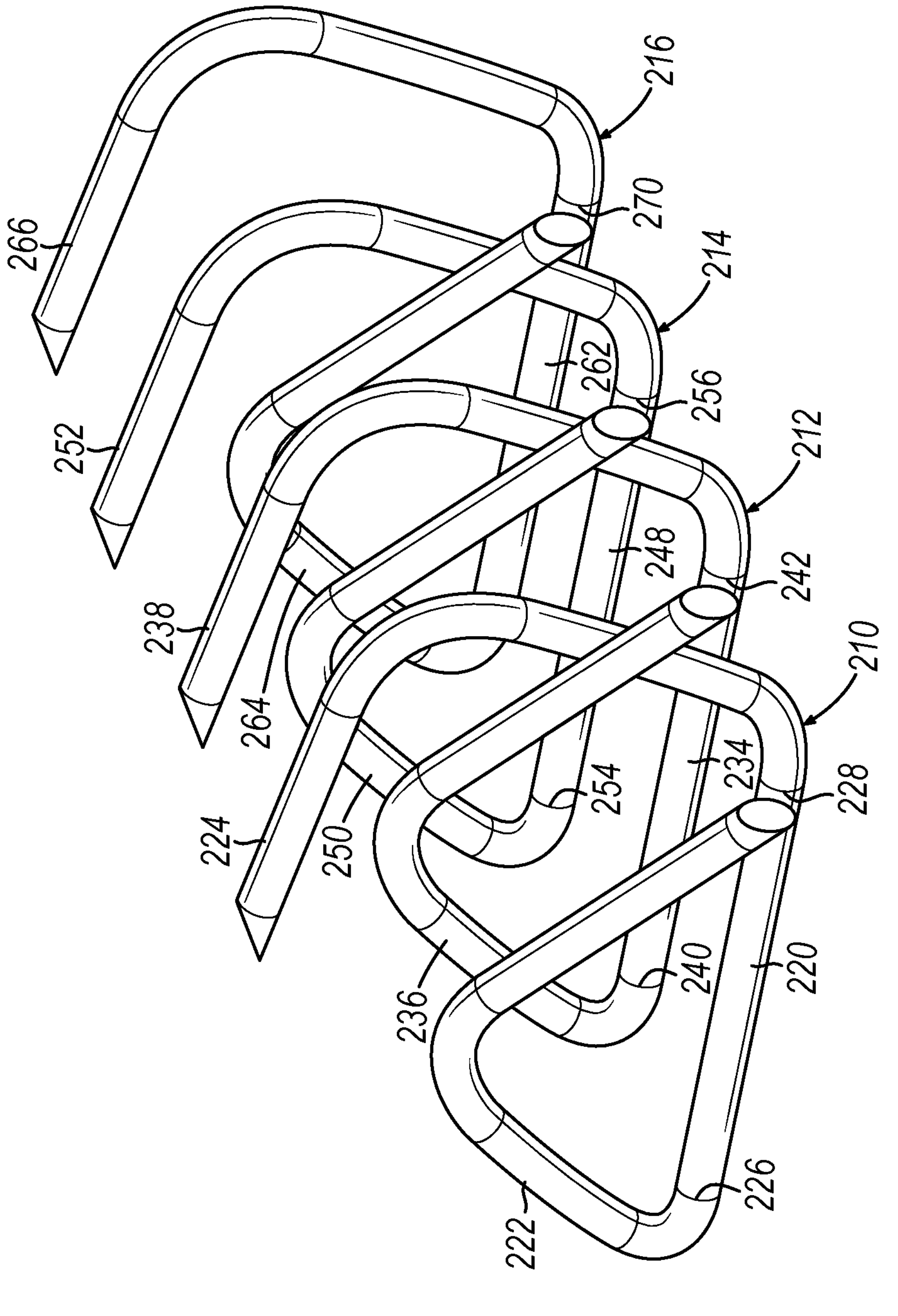
FIG. 16 depicts a perspective view of the staples of FIG. 12B.

In the deformed state shown in FIGS. 12B, 13B, 14B, 15C-18, first leg (222, 236, 250, 264) and second leg (224, 238, 252, 266) may be bent. In other words, in the deformed state, first and second legs (222, 224, 236, 238, 250, 252, 264, 266) terminate at third and fourth distances (D3, D4) away from an upper surface of first and second crowns (220, 234). While third and fourth distances (D3, D4) are shown in FIG. 13B as being equal, third and fourth distances (D3, D4) may be different. As shown in the deformed state of FIGS. 12B, 13B, 14B, 15C-18, first legs (222, 236, 250, 264) extend generally parallel to one another. Similarly, second leg (224, 238, 252, 266) of first, second, third, and fourth staples (210, 212, 214, 216) extend generally parallel to one another and approximately 180 degrees opposite first legs (222, 236). As shown in FIGS. 12B and 16, first and second legs (222, 224, 236, 238, 250, 252, 264, 266) each include first and second bent portions that extend at an angle relative to each other. While first, second, third, and fourth staples (210, 212, 214, 216) are not shown as being in direct contact with each other, first, second, third, and fourth staples (210, 212, 214, 216) appear interleaved together. Staple drivers (not shown), but which may be similar to staple drivers (43), are configured to contact first, second, third, and fourth crowns (220, 234, 248, 262) may and drive first, second, third, and fourth crowns (220, 234, 248, 262) may toward the anvil (218). First, second, third, and fourth crowns (220, 234, 248, 262) may extend parallel to one another in each of the non-deformed and deformed states. As shown, second crown (234) is parallel to and offset from first crown (220) by a fixed distance. The fixed distance is the same for the non-deformed and deformed states.

Figure 17:
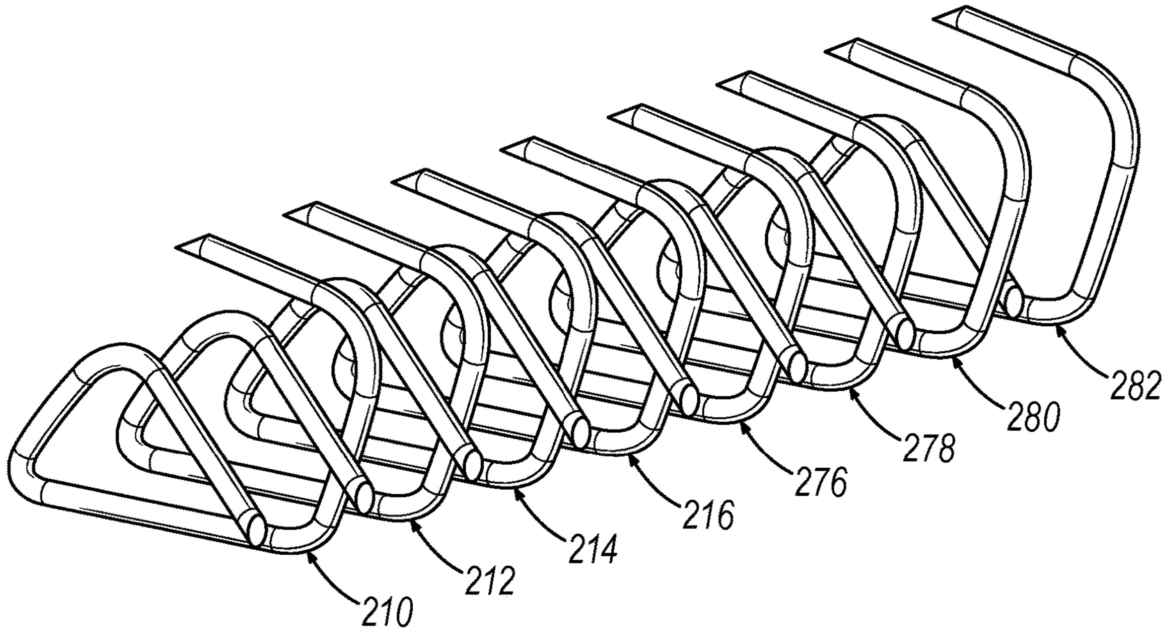
FIG. 17 depicts a perspective view of an arrangement of staples including the staples of FIG. 12B.
Figure 18:
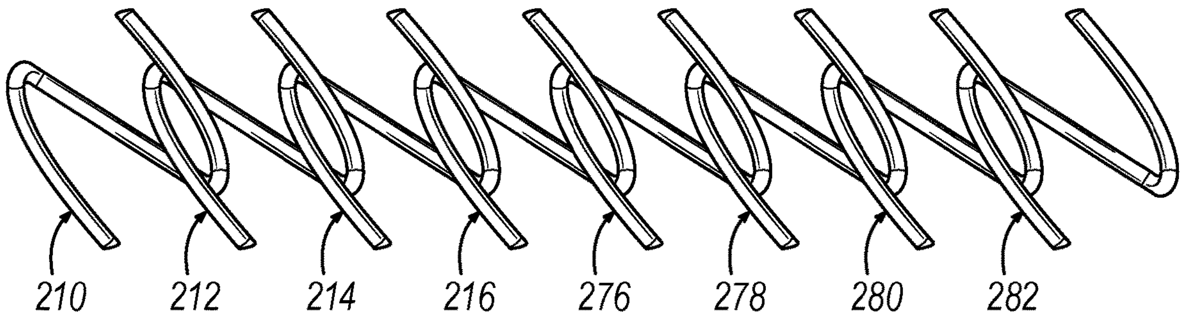
FIG. 18 depicts a top view of the arrangement of staples of FIG. 17.

FIGS. 17 and 18 show first, second, third, and fourth staples (210, 212, 214, 216) of FIGS. 12A-16 as well as fifth, sixth, seventh, and eighth staples (276, 278, 280, 282). This illustrates this overlapping pattern may continue with additional staples where legs of adjacent staples are disposed over crowns. The overlap of first, second, third, and fourth, fifth, sixth, seventh, and eighth staples (210, 212, 214, 216, 276, 278, 280, 282) may increase robustness and strength of the staple line as a whole (formed by first, second, third, and fourth staples (210, 212, 214, 216) and may allow for increased staple density.

Figure 19:
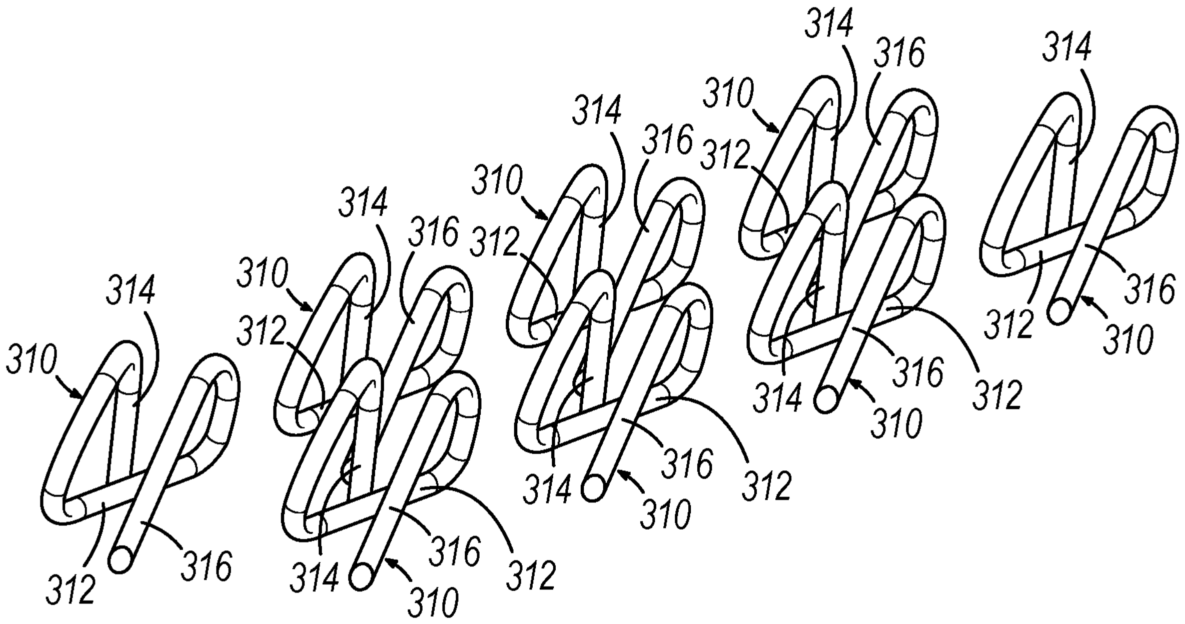
FIG. 19 depicts a perspective view of non-overlapping staples in a deformed state that are spaced apart from one another.
Figure 20:
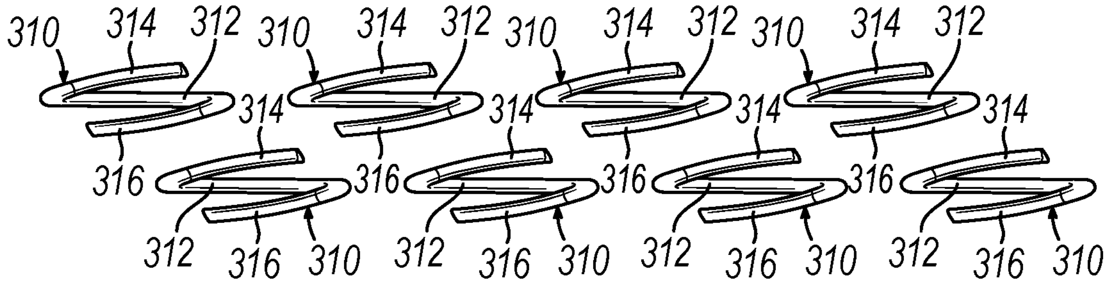
FIG. 20 depicts a top view of the plurality of staples of FIG. 19.

FIGS. 19 and 20 show perspective and top views of exemplary staples (310) that are different than first, second, third, and fourth staples (210, 212, 214, 216) described above. Staples (310) each include a crown (312) with first and second legs (314, 316) extending from crown (312). As shown in FIG. 20, in the deformed state, staples (310) are separated from each another and generally form an S shape.

C. Second Exemplary Alternative Anvil

Figure 21:
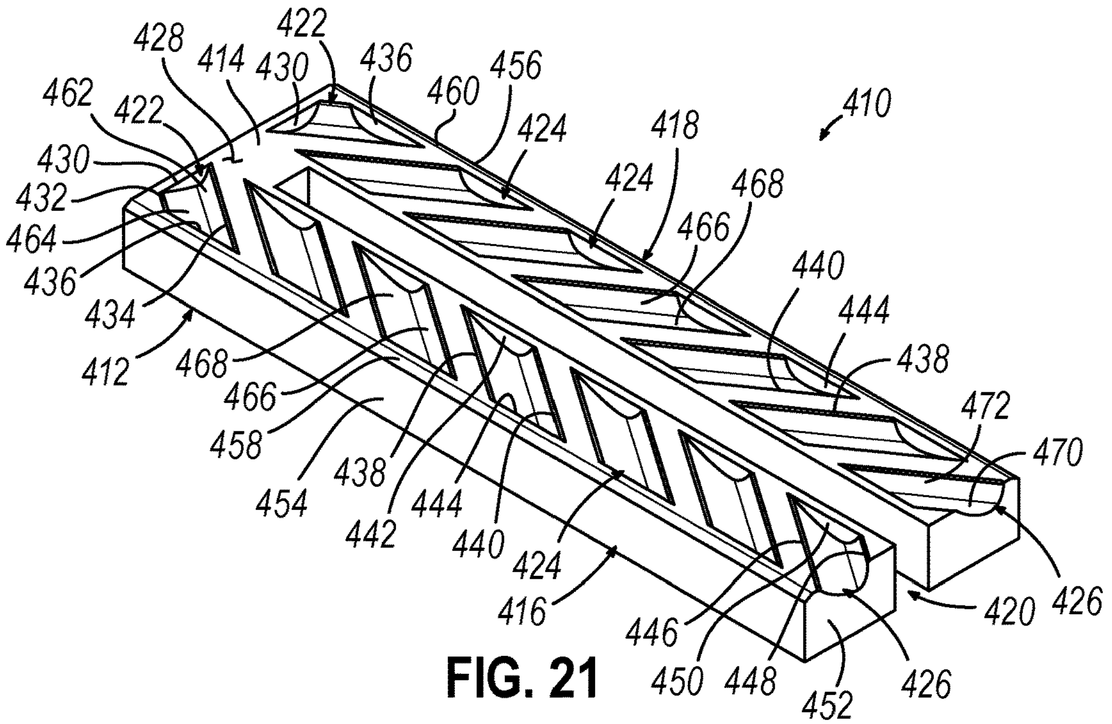
FIG. 21 depicts a perspective view of a second exemplary alternative anvil that may be incorporated into the instrument of FIG. 1.
Figure 22:
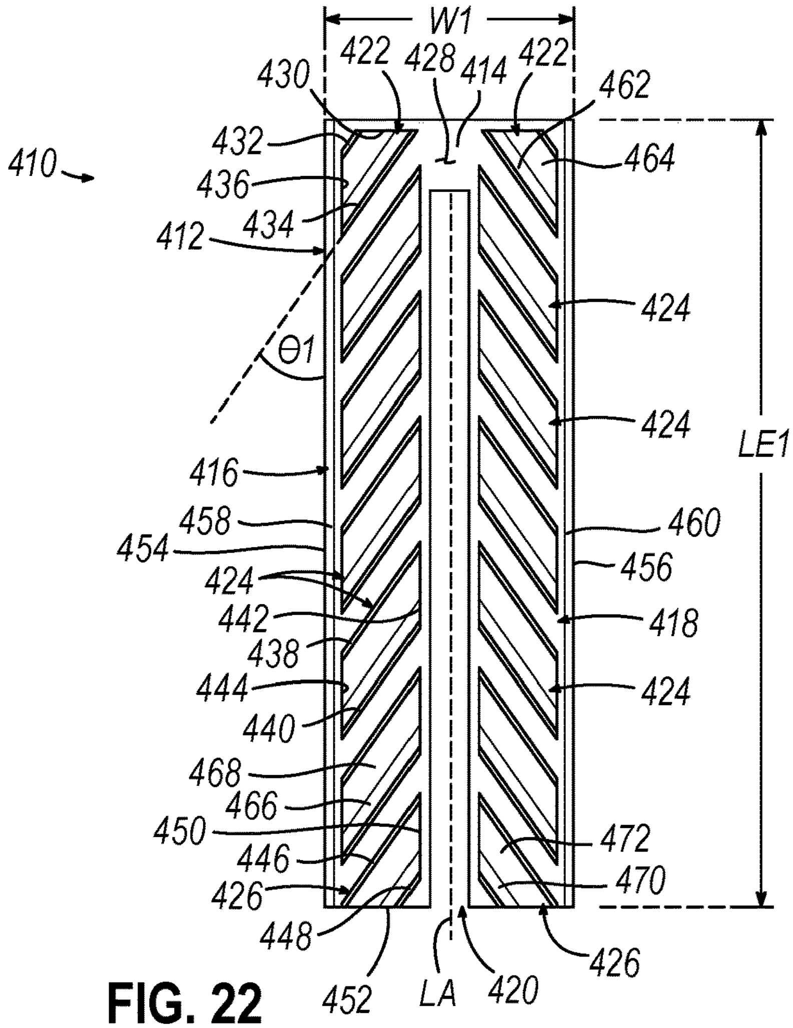
FIG. 22 depicts a top view of the anvil of FIG. 21.

FIGS. 21-22 show a second exemplary alternative anvil (410) that may be incorporated into the instrument (10) of FIG. 1. Anvil (410) includes a body (412), which is shown as being integrally formed together as a unitary piece. Body (412) includes a distal connecting portion (414), a first lateral portion (416), and a second lateral portion (418). First and second lateral portions (416, 418) are separated by a longitudinal slot (420) that is configured to receive a knife (not shown), but which may be similar to distally presented cutting edge (48) of firing beam (14) described above. Anvil (410) is shown as being symmetric about longitudinal slot (420).

Staple forming pockets (422, 424, 426) are disposed at an angle (θ1) relative to longitudinal axis (LA). Angle (θ1) may vary. Staple forming pockets (422, 424, 426) slightly angled relative to axis of longitudinal slot (420). Anvil (410) includes distal, central, and proximal staple forming pockets (422, 424, 426) formed in an upper surface (428) of body (412). Distal staple forming pockets (422) include a distal wall (430), first and second angled walls (432, 434), and an outer wall (436). Central staple forming pockets (424) include first and second angled walls (438, 440) and inner and outer walls (442, 444). Proximal staple forming pockets (426) include first and second angled walls (446, 448), an inner wall (450), and open into a proximal end (452) of body (412). First and second angled walls (432, 434, 438, 440, 446, 448) of distal, central, and proximal staple forming pockets (422, 424, 426) extend at angle (θ1) relative to longitudinal axis (LA). Inner walls (442, 450) and outer wall (444) extend parallel to longitudinal axis (LA). First and second outer lateral walls (454, 456) include tapered outer edges (458, 460). Distal staple forming pockets (422) include a higher slope region (462) and a lower slope region (464). Similarly, central staple forming pockets (424) include a higher slope region (466) and a lower slope region (468) and proximal staple forming pockets (426) include a higher slope region (470) and a lower slope region (472). Higher slope regions (462, 466, 470) have a slope that is greater than lower slope regions (464, 468, 472).

For anvil (410), multiple staples (e.g., staples (110, 112, 210, 212, 214, 216, 276, 278, 280, 282)) may be formed in each staple forming pockets (422, 424, 426). As a result, there may not a 1:1 correlation between staple forming pockets (422, 424, 426) and staples (110, 112, 210, 212, 214, 216, 276, 278, 280, 282). In other words, the number of staples (110, 112, 210, 212, 214, 216, 276, 278, 280, 282) may exceed the number of staple forming pockets (422, 424, 426). Anvil (410) may reduce cost of construction, as staple forming pockets (422, 424, 426) including staple forming pockets (422, 424, 426) that include continuous channels are more inexpensive to manufacture was well as to inspect and qualify. Anvil (410) may allow for increased staple leg density along length (LE1) of anvil (410). Higher staple density may provide increased seal strength against luminal leakage. Anvil (410) may decrease the width (W1) of anvil (410) compared to other layouts of staple forming pockets. Anvil (410) may also reduce the risk associated tipping of staples (110, 112, 210, 212, 214, 216, 276, 278, 280, 282) when moving to the deformed state while still allowing for crossover of adjacent legs (122, 124, 136, 138, 222, 224, 236, 238, 250, 252, 264, 266) relative to crowns (120, 134, 220, 234, 248, 262).

D. Third Exemplary Alternative Anvil

Figure 23:
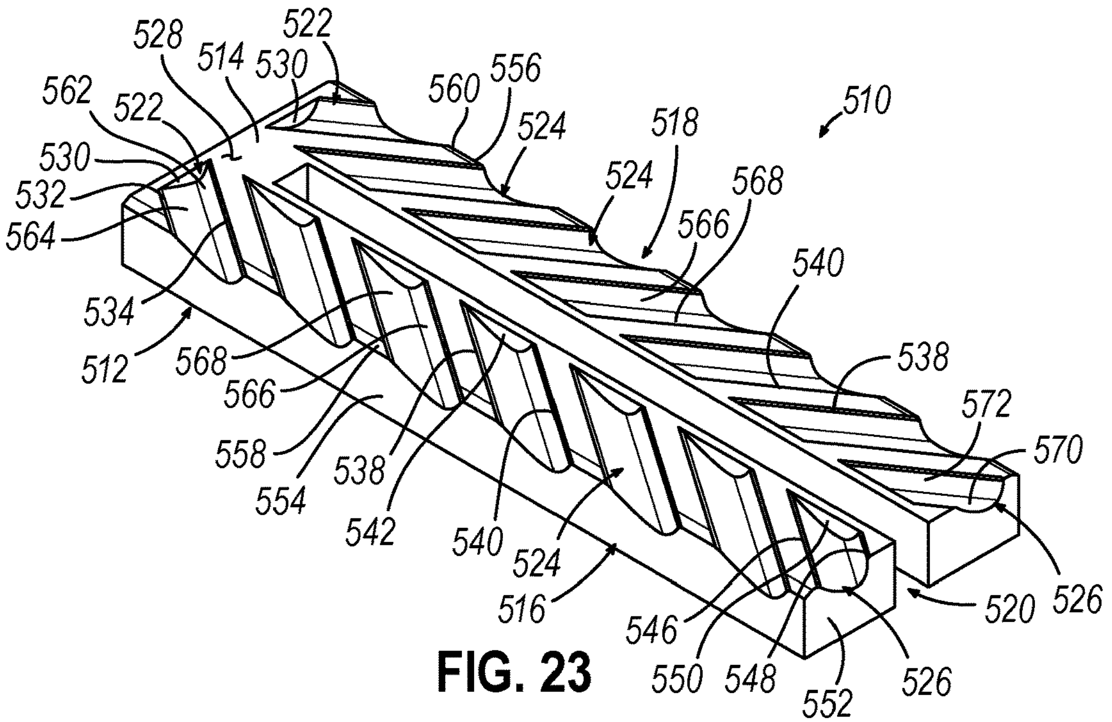
FIG. 23 depicts a perspective view of a third exemplary alternative anvil that may be incorporated into the instrument of FIG. 1.
Figure 24:
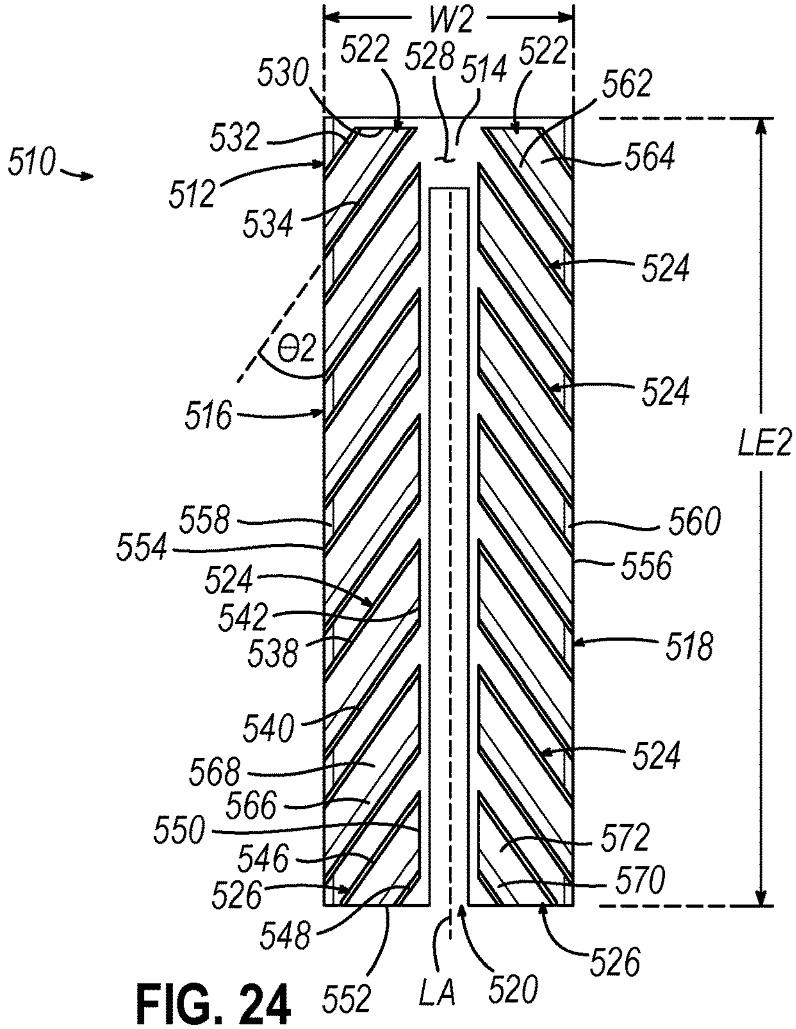
FIG. 24 depicts a top view of the anvil of FIG. 23.

FIGS. 23-24 show a third exemplary alternative anvil (510) that may be incorporated into the instrument (10) of FIG. 1. Anvil (510) is similar to anvil (410) described above. Anvil (510) includes a body (512). Body (512) includes a distal connecting portion (514), a first lateral portion (516), and a second lateral portion (518). First and second lateral portions (516, 518) are separated by a longitudinal slot (520). Anvil (510) is shown as being symmetric about longitudinal slot (520).

Staple forming pockets (522, 524, 526) are disposed at an angle (θ2) relative to longitudinal axis (LA). Angle (θ2) may vary. Staple forming pockets (522, 524, 526) slightly angled relative to axis of longitudinal slot (520). Anvil (510) includes distal, central, and proximal staple forming pockets (522, 524, 526) formed in an upper surface (528) of body (512). Distal staple forming pockets (522) include a distal wall (530) and first and second angled walls (532, 534). Central staple forming pockets (524) include first and second angled walls (538, 540) and inner walls (542). Proximal staple forming pockets (526) include first and second angled walls (546, 548), an inner wall (550), and open into a proximal end (552) of body (512). First and second outer lateral walls (554, 556) include tapered outer edges (558, 560). Unlike outer walls (436, 444) of distal and central staple forming pockets (422, 424) described above with reference to FIGS. 20-21, staple forming pockets (522, 524) open directly into first and second outer lateral walls (554, 556) and do not include outer walls (436, 444) of distal and central staple forming pockets (422, 424).

First and second angled walls (532, 534, 538, 540, 546, 548) of distal, central, and proximal staple forming pockets (522, 524, 526) extend at angle (θ2) relative to longitudinal axis (LA). Inner walls (542, 550) and outer wall (544) extend parallel to longitudinal axis (LA). Distal staple forming pockets (522) include a higher slope region (562) and a lower slope region (564). Similarly, central staple forming pockets (524) include a higher slope region (566) and a lower slope region (568) and proximal staple forming pockets (526) include a higher slope region (570) and a lower slope region (572). For anvil (510), multiple staples (e.g., staples (110, 112, 210, 212, 214, 216, 276, 278, 280, 282)) may be formed in each staple forming pockets (522, 524, 526). As a result, there may not a 1:1 correlation between staple forming pockets (522, 524, 526) and staples (110, 112, 210, 212, 214, 216, 276, 278, 280, 282). In other words, the number of staples (110, 112, 210, 212, 214, 216, 276, 278, 280, 282) may exceed the number of staple forming pockets (522, 524, 526). Anvil (510) may reduce cost of construction as well as be more easily inspected and qualified. Anvil (510) may allow for increased staple leg density along length (LE2) of anvil (510). Higher staple density may provide increased seal strength against luminal leakage. Anvil (510) may decrease the width (W2) of anvil (510) compared to other layouts of staple forming pockets. Anvil (510) may also reduce the risk associated tipping of staples (110, 112, 210, 212, 214, 216, 276, 278, 280, 282) when moving to the deformed state while still allowing for crossover of adjacent legs (122, 124, 136, 138, 222, 224, 236, 238, 250, 252, 264, 266) relative to crowns (120, 134, 220, 234, 248, 262).

E. Exemplary Circular Surgical Stapler with Fourth Exemplary Alternative Anvil

Figure 25:
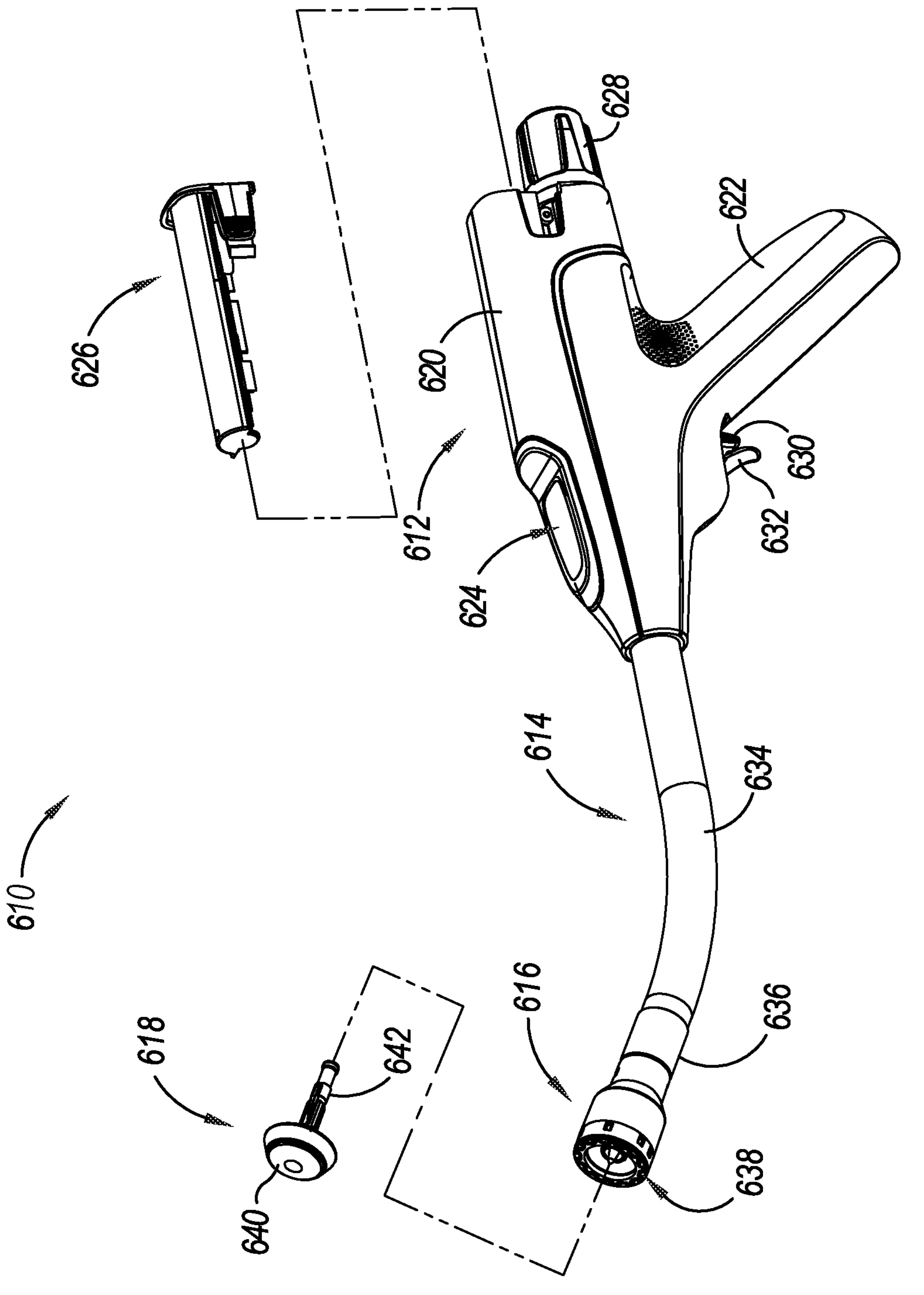
FIG. 25 depicts a perspective view of an exemplary circular surgical stapler, with a battery pack removed from a handle assembly and an anvil assembly removed from a stapling head assembly.

FIG. 25 depicts an exemplary circular surgical stapler (610) that may be used to provide an end-to-end, side-to-side, or end-to-side anastomosis between two sections of an anatomical lumen such as a portion of a patient's digestive tract. Circular surgical stapler (610) of this example comprises a handle assembly (612), a shaft assembly (614), a stapling head assembly (616), and an anvil assembly (618). Handle assembly (612) comprises a casing (620) defining an obliquely oriented pistol grip (622). In some versions, pistol grip (622) is perpendicularly oriented. In some other versions, pistol grip (622) is omitted. Handle assembly (612) further includes a user feedback feature (624) that permits viewing of a movable indicator needle (not shown). Circular surgical stapler (610) includes a battery pack (626). Battery pack (626) is operable to provide electrical power to a motor (not shown). Shaft assembly (614) extends distally from handle assembly (612) and includes a preformed bend, which may facilitate positioning of stapling head assembly (616) within a patient's colon.

Stapling head assembly (616) is located at the distal end of shaft assembly (614). As shown, anvil assembly (618) is configured to removably couple with shaft assembly (614), adjacent to stapling head assembly (616). Anvil assembly (618) and stapling head assembly (616) are configured to cooperate to manipulate tissue in three ways, including clamping the tissue, cutting the tissue, and stapling the tissue. A knob (628) at the proximal end of handle assembly (612) is rotatable relative to casing (620) to provide precise clamping of the tissue between anvil (618) and stapling head assembly (616). When a safety trigger (630) of handle assembly (612) is pivoted away from a firing trigger (632) of handle assembly (612), firing trigger (632) may be actuated to provide cutting and stapling of the tissue. Stapling head assembly (616) of the present example is coupled to a distal end of shaft assembly (614) and comprises a body member (634) and a slidable staple driver member (not shown). Body member (634) includes a distally extending cylindraceous inner core member (not shown). Body member (634) is fixedly secured to an outer sheath (636) of shaft assembly (200). A deck member (638) is fixedly secured to body member (634), and includes a distally presented deck surface (not shown) defining two concentric annular arrays of staple openings. Anvil assembly (618) includes a head (640) and a shank (642).

Figure 26:
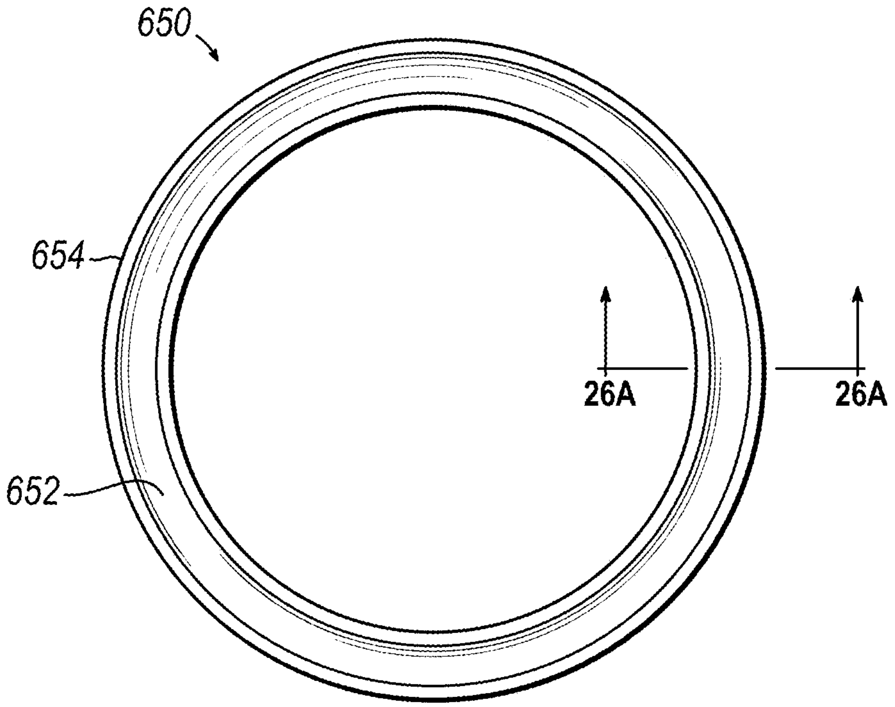
FIG. 26 depicts a top view of a fourth exemplary alternative anvil for use with anvil assembly of FIG. 25.
Figure 26A:
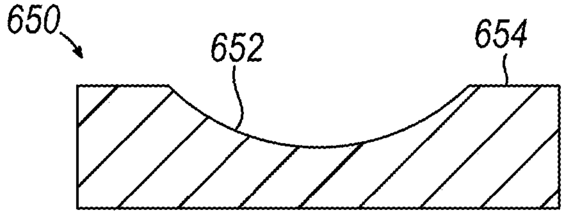
FIG. 26A depicts cross-sectional view of the anvil of FIG. 26 taken along line 26A-26A of FIG. 26.

FIGS. 26-26A show a fourth exemplary alternative anvil (650) that may be incorporated into head (640) of anvil assembly (618) of circular surgical stapler (610) shown in FIG. 25. Anvil (650) may be used in conjunction with third exemplary alternative staples (710) of FIG. 27 described below. The principles of anvil (650) and staples (710) may be provided in accordance with one or more teachings of U.S. application Ser. No. 17/401,391, entitled "Methods of Forming an Anastomosis Between Organs with an Expandable Staple Pattern," filed Aug. 13, 2021, issued as U.S. Pat. No. 12,256,934 on Mar. 25, 2025, the disclosure of which is incorporated by reference herein in its entirety. The principles of anvil (650) and staples (710) may be provided in accordance with one or more teachings of U.S. Pub. No. 2018/0132849, entitled "Staple Forming Pocket Configurations for Circular Surgical Stapler Anvil," published May 17, 2018, now Abandoned; U.S. Pub. No. 2020/0038017, entitled "Surgical End Effectors with Staple Cartridges," published Feb. 6, 2020, issued as U.S. Pat. No. 11,406,379 on Jul. 20, 2022; and/or U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein in its entirety.

Anvil (650) is shown as being annular. Anvil (650) includes at least one annular staple forming pocket (652) formed in an upper surface (654) of anvil (650). While only one annular staple forming pocket (652) is shown, additional staple forming pockets are also envisioned, which may or may not be annular. For example, annular staple forming pocket (652) may be combined with another annular staple forming pocket (652) and/or another non-annular staple forming pocket. While annular staple forming pocket (652) is shown as being U-shaped in sectional view of FIG. 26A, annular staple forming pocket (652) may have a variety of suitable shapes. Similar to anvils (410, 510), annular staple forming pocket (652) is configured to interact with multiple staples (e.g., staples (110, 112, 210, 212, 214, 216, 276, 278, 280, 282)). In other words, for anvil (650), multiple staples (e.g., staples (110, 112, 210, 212, 214, 216, 276, 278, 280, 282)) may be formed using annular staple forming pocket (652). Anvil (650) may reduce cost of construction, as annular staple forming pocket (652) is more cost effective to produce, to inspect, and to qualify than other staple forming pockets having a 1:1 correlation with respective staples. Anvil (650) may allow for increased staple leg density. Higher staple density may provide increased seal strength against luminal leakage.

F. Third Exemplary Alternative Staples

Figure 27:
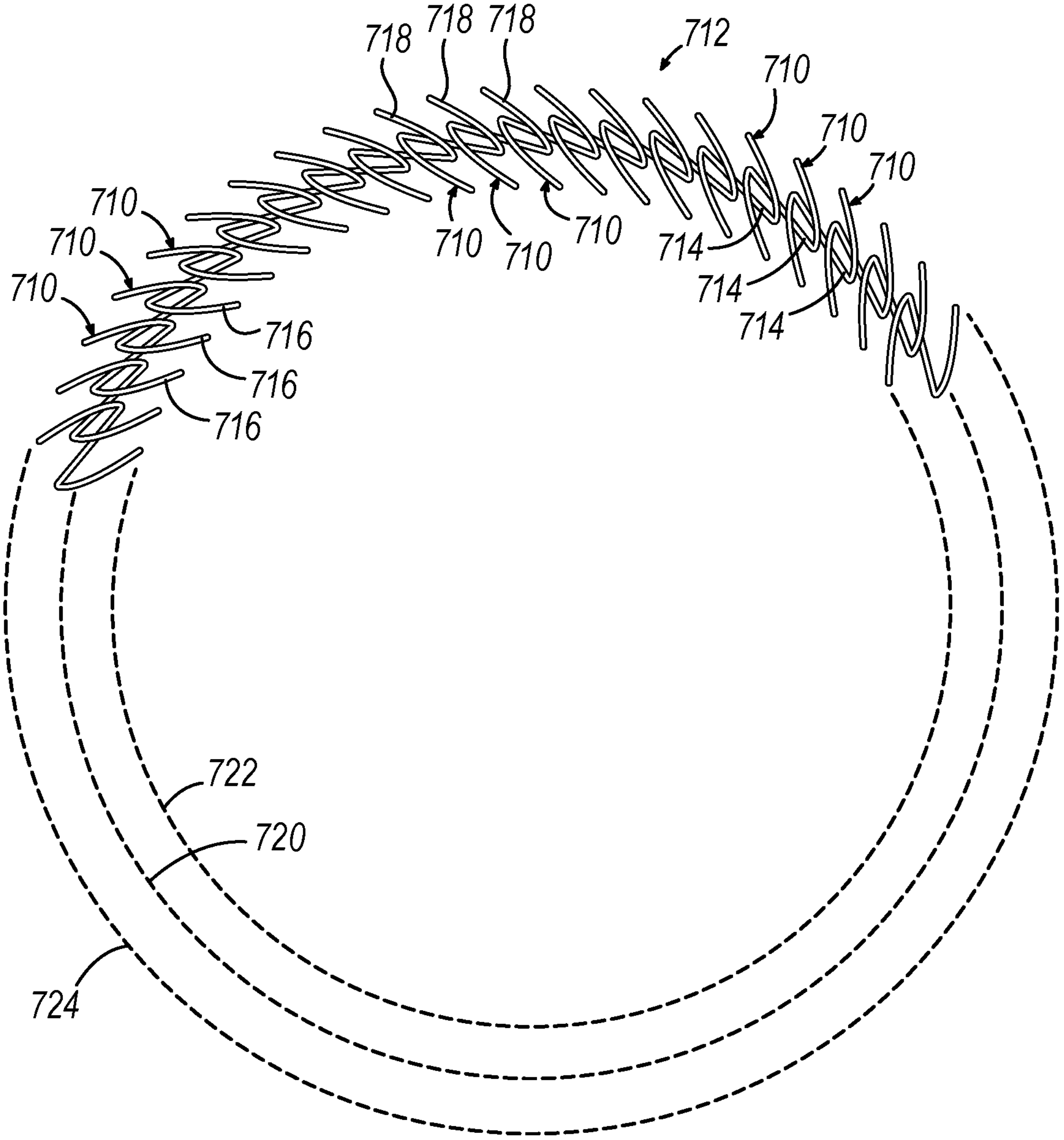
FIG. 27 depicts a top view of third exemplary alternative staples in a deformed state, where the staples may be incorporated into a circular surgical stapler.

FIG. 27 shows third exemplary alternative staples (710) in a deformed state, where the staples (710) may be incorporated into stapling head assembly (616) of circular surgical stapler (610) of FIG. 25. Staples (710) may be similar to staples (110, 112, 210, 212, 214, 216, 276, 278, 280, 282) described above with reference to FIGS. 8A-18. Adjacent staples (710) overlap in a similar manner to staples (110, 112, 210, 212, 214, 216, 276, 278, 280, 282) described above in detail. However, unlike staples (110, 112, 210, 212, 214, 216, 276, 278, 280, 282), staples (710) are arranged in an annular arrangement (712), also referred to as an annular array, for use with stapling head assembly (616) of circular surgical stapler (610). Staples (710) each include a crown (714) with first and second legs (716, 718) extending from crown (714) similar to staples (110, 112, 210, 212, 214, 216, 276, 278, 280, 282). Staples (710) may be loaded into a stapling assembly in a manner allowing for first and second legs (716, 718) to be oriented obliquely to cross over crowns (714) of adjacent staples (710). Staples (710) may be arranged to define a center line (720). In the deformed state, first legs (716) of staples (710) may define an innermost annular point (722) and second legs (718) may define an outermost annular point (724).

EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument, comprising: (a) an anvil; and (b) a stapling assembly comprising: (i) a first staple that includes a first crown, and (ii) a second staple, wherein the anvil is configured to deform the first and second staples to thereby transition the first and second staples from a non-deformed state to a deformed state, the second staple comprising: (A) a second crown, and (B) a first leg disposed at a first angle relative to the second crown in the non-deformed state, wherein the first leg of the second staple is configured to extend over the first crown to form an overlapping staple pattern between the first and second staples when the first and second staples are in the deformed state.

Example 2

The surgical stapling instrument of Example 1, wherein the first staple further comprises a leg disposed at an angle relative to the first crown in the non-deformed state, wherein the leg of the first staple is configured to extend over the second crown to form an overlapping staple pattern between the first and second staples when the first and second staples are in the deformed state.

Example 3

The surgical stapling instrument of any one or more of Examples 1 through 2, wherein the stapling assembly further comprises a third staple, wherein the anvil is configured to deform the third staple from a non-deformed state to a deformed state, the third staple comprising: (A) a third crown, and (B) a leg disposed at a first angle relative to the third crown in the non-deformed state, wherein the leg of the third staple is configured to extend over the second crown to form an overlapping staple pattern between the second and third staples are in the deformed state.

Example 4

The surgical stapling instrument of Example 3, wherein the second staple further comprises a second leg disposed at a second angle relative to the second crown in the non-deformed state, wherein the second leg is configured to extend over the third crown to form an overlapping staple pattern between the second and third staples are in the deformed state.

Example 5

The surgical stapling instrument of Example 4, wherein the first and second angles of the first and second legs of the second staple are equal.

Example 6

The surgical stapling instrument of any one or more of Example 4 through 5, wherein the first and second legs are straight in the non-deformed state.

Example 7

The surgical stapling instrument of any one or more of Examples 4 through 6, wherein the stapling assembly further comprises a fourth staple, wherein the anvil is configured to deform the fourth staple to thereby transition the fourth staple from a non-deformed state to a deformed state, the fourth staple comprising: (A) a fourth crown, and (B) a leg disposed at a first angle relative to the fourth crown in the non-deformed state, wherein the leg of the fourth staple is configured to extend over the third crown of the third staple to form an overlapping staple pattern between the third and fourth staples are in the deformed state.

Example 8

The surgical stapling instrument of any one or more of Examples 1 through 7, wherein the stapling assembly extends along in a longitudinal direction, wherein the first leg of the second staple is spaced a distance from the longitudinal direction from the first crown in the non-deformed state, wherein in the deformed state the first leg of the second staple is configured to occupy a space between the first crown and the anvil.

Example 9

The surgical stapling instrument of any one or more of Example 1 through 8, wherein the first and second crowns are configured to extend parallel to each another in the non-deformed and deformed states.

Example 10

The surgical stapling instrument of any one or more of Examples 1 through 9, wherein the first staple is discrete from the second staple in the non-deformed and deformed states.

Example 11

The surgical stapling instrument of any one or more of Examples 1 through 10, further comprising a first staple driver configured to contact the first crown and drive the first crown toward the anvil.

Example 12

The surgical stapling instrument of any one or more of Examples 1 through 11, wherein the anvil includes a staple forming pocket, wherein the staple forming pocket is configured deform of the first and second staples to thereby transition the first and second staples from the non-deformed state to the deformed state.

Example 13

The surgical stapling instrument of any one or more of Examples 1 through 12, wherein the stapling assembly extends along a longitudinal axis, wherein the staple forming pocket is disposed at an oblique angle relative to the longitudinal axis of the stapling assembly.

Example 14

The surgical stapling instrument of any one or more of Examples 1 through 7, and Examples 7 through 10, further comprising an annular array of staples that include the first and second staples.

Example 15

The surgical stapling instrument of Example 14, wherein the anvil includes an annular anvil having a single annular staple forming pocket to interact with the annular array of staples.

Example 16

A surgical stapling instrument, comprising: (a) an anvil that includes a staple forming pocket; and (b) a stapling assembly comprising: (i) a first staple comprising: (A) a first crown, (B) a first leg extending from the first crown, and (C) a second leg extending from the first crown, and (ii) a second staple, wherein the staple forming pocket of the anvil is configured to deform the first and second staples from a non-deformed state to a deformed state, the second staple comprising: (A) a second crown, and (B) a leg extending at a first angle relative to the second crown in the non-deformed state, wherein the leg of the second staple is configured to extend over the first crown to form an overlapping staple pattern between the first and second staples when the first and second staples are in the deformed state.

Example 17

The surgical stapling instrument of Example 16, further comprising an annular array of staples that includes the first and second staples.

Example 18

The surgical stapling instrument of any one or more of Examples 16 through 17, wherein the second leg of the first staple is configured to extend over the second crown to form an overlapping staple pattern between the first and second staples when the first and second staples are in the deformed state.

Example 19

A method of operating a surgical stapling instrument comprising: actuating a stapling assembly of the surgical stapling instrument to drive first and second staples from a non-deformed state in which a leg of the second staple is separated by a distance from the first staple to a deformed state in which the leg of the second staple overlaps a crown of the first staple to form an overlapping staple pattern with the first and second staples.

Example 20

The method of Example 19, wherein actuating the stapling assembly further comprises driving the first and second staples from the non-deformed state in which a leg of the first staple is separated by a distance from the second staple to a deformed state in which the leg of the first staple overlaps a crown of the second staple to form the overlapping staple pattern with the first and second staples.

MISCELLANEOUS

Any one or more of the teachings, expressions, embodiments, examples, etc. described herein may be combined with any one or more of the teachings, expressions, embodiments, examples, etc. described in U.S. patent application Ser. No. 17/401,391, entitled "Staple and Staple-Forming Pocket Arrangements for Surgical Staplers," filed on Aug. 13, 2021, the disclosure of which is incorporated by reference herein.

The teachings of this application may be applied to anvils of all types of surgical staplers, including endocutters, linear surgical staplers, circular surgical staplers, right angle surgical staplers, and curved surgical staplers, for example. For example, the teachings of this application may be combined with various exemplary linear surgical staplers, such that those shown and described in U.S. Pat. No. 11,045,193, entitled "Anvil Assembly for Linear Surgical Stapler," issued Jun. 29, 2021, the disclosure of which is incorporated by reference herein in its entirety. The teachings of this application may be combined with various exemplary circular surgical staplers, such that those shown and described in U.S. Pat. No. 10,709,452, entitled "Methods and Systems for Performing Circular Stapling," issued Jul. 14, 2020, the disclosure of which is incorporated by reference herein in its entirety. The teachings of this application may be combined with various exemplary right angle surgical staplers, such that those shown and described in U.S. Pub. No. 2020/0337698, entitled "Tissue Cutting Washer for Right Angle Surgical Stapler," published Oct. 29, 2020, issued as U.S. Pat. No. 11,266,403 on Mar. 8, 2022, the disclosure of which is incorporated by reference herein in its entirety. The teachings of this application may be combined with various exemplary curved surgical staplers, such that those shown and described in U.S. application Ser. No. 16/945,042, entitled "Features to Enhance Staple Height Consistency in Curved Surgical Stapler," filed Jul. 31, 2020, issued as U.S. Pat. No. 11,432,815 on Aug. 17, 2022, the disclosure of which is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling instrument, comprising:

(a) an anvil includes a staple forming pocket, wherein the staple forming pocket extends along a longitudinal axis; and (b) a stapling assembly comprising:

(i) a first staple that includes a first crown, wherein the first crown extends along a first axis, and (ii) a second staple, wherein the staple forming pocket of the anvil is configured to deform each of the first and second staples to thereby transition the first and second staples from a non-deformed state where the second staple extends along a first plane to a deformed state where the second staple extends along multiple planes including the first plane, the second staple comprising:

(A) a second crown that is generally parallel to and offset from the first crown by a fixed distance, wherein the fixed distance is the same for the non-deformed and deformed states, wherein the second crown extends along a second axis, wherein the first and second axes each extend substantially at a same angle relative to the longitudinal axis in response to being transitioned to the deformed state, (B) a first leg extending from the second crown and terminating at a first end, wherein the first leg is disposed at a first angle relative to the second crown in the non-deformed state, wherein the first leg of the second staple is configured to extend over the first crown such that the first leg extends into a space directly between the first crown and the anvil to form an overlapping staple pattern between the first and second staples in response to the first and second staples being transitioned to the deformed state, and (C) a second leg extending from the second crown and terminating at a second end, wherein the first and second ends of the second staple are separated by a first distance in the non-deformed state, wherein the first and second ends of the second staple are separated by a second distance in the deformed state, wherein the second distance is greater than the first distance, wherein the first and second staples form an interlocking shape in the deformed state, wherein first and second ends are deformed in opposite directions away from the longitudinal axis.

2. The surgical stapling instrument of claim 1, wherein the first staple further comprises a leg disposed at an angle relative to the first crown in the non-deformed state, wherein the leg of the first staple is configured to extend over the second crown in a space between the second crown and the anvil to form an overlapping staple pattern between the first and second staples in response to the first and second staples being transitioned to the deformed state.

3. The surgical stapling instrument of claim 1, wherein the stapling assembly further comprises a third staple, wherein the anvil is configured to deform the third staple from a non-deformed state to a deformed state, the third staple comprising:

(A) a third crown, and (B) a leg disposed at a first angle relative to the third crown in the non-deformed state, wherein the leg of the third staple is configured to extend over the second crown in a space between the second crown and the anvil to form an overlapping staple pattern between the second and third staples in response to the second and third staples being transitioned to the deformed state.

4. The surgical stapling instrument of claim 3, wherein the second leg is disposed at a second angle relative to the second crown in the non-deformed state, wherein the second leg is configured to extend over the third crown in a space directly between the third crown and the anvil to form an overlapping staple pattern between the second and third staples in response to the second and third staples being transitioned to the deformed state.

5. The surgical stapling instrument of claim 4, wherein the first and second angles of the first and second legs of the second staple are equal.

6. The surgical stapling instrument of claim 4, wherein the stapling assembly further comprises a fourth staple, wherein the anvil is configured to deform the fourth staple to thereby transition the fourth staple from a non-deformed state to a deformed state, the fourth staple comprising:

(A) a fourth crown, and (B) a leg disposed at a first angle relative to the fourth crown in the non-deformed state, wherein the leg of the fourth staple is configured to extend over the third crown of the third staple in a space directly between the third crown and the anvil to form an overlapping staple pattern between the third and fourth staples in response to the third and fourth staples being transitioned to the deformed state.

7. The surgical stapling instrument of claim 1, wherein the stapling assembly extends along in a longitudinal direction, wherein the first leg of the second staple is spaced a distance from the longitudinal direction from the first crown in the non-deformed state, wherein the space extends along a plane that is perpendicular to the longitudinal direction between the first crown and the anvil.

8. The surgical stapling instrument of claim 1, wherein the first staple is discrete from the second staple in the non-deformed and deformed states.

9. The surgical stapling instrument of claim 1, wherein the anvil extends along a longitudinal axis, wherein the staple forming pocket of the anvil is disposed at an oblique angle relative to the longitudinal axis of the anvil.

10. The surgical stapling instrument of claim 1, wherein the first and second ends define a maximum distance between the first and second legs of the second staple in the deformed state.

11. The surgical stapling instrument of claim 1, wherein the first and second staples form an interlocking S shape in the deformed state.

12. A surgical stapling instrument, comprising:

(a) an anvil that includes a staple forming pocket, wherein the staple forming pocket extends along a longitudinal axis; and (b) a stapling assembly comprising:

(i) a first staple comprising:

(A) a first crown extending along a first axis, (B) a first leg extending from the first crown and terminating at a first end, and (C) a second leg extending from the first crown and terminating at a second end, and (ii) a second staple, wherein the staple forming pocket of the anvil is configured to deform each of the first and second staples from a non-deformed state to a deformed state, wherein the first crown and the first leg, while in the non-deformed state, define a plane, the second staple comprising:

(A) a second crown extending along a second axis, wherein the first and second axes each extend substantially at a same angle relative to the longitudinal axis in response to being transitioned to the deformed state, and (B) a leg extending at a first angle relative to the second crown in the non-deformed state, wherein the leg of the second staple is configured to extend over the first crown in the plane to form an overlapping staple pattern between the first and second staples in response to the first and second staples being transitioned to the deformed state, wherein the first and second ends of the first staple are separated by a first distance in the non-deformed state, wherein the first and second ends of the first staple are separated by a second distance in the deformed state, wherein the second distance is greater than the first distance, wherein the first and second staples form an interlocking shape in the deformed state, wherein the first and second ends are deformed in opposite directions away from the longitudinal axis.

13. The surgical stapling instrument of claim 12, wherein the second leg of the first staple is configured to extend over the second crown to form the overlapping staple pattern between the first and second staples in response to the first and second staples being transitioned to the deformed state.

14. The surgical stapling instrument of claim 12, wherein the second crown and the leg in the non-deformed state define a second plane that is offset from and generally parallel to the first plane in the non-deformed state, wherein the first crown is in the first plane in the deformed state and the second crown is in the second plane in the deformed state.

15. A surgical stapling instrument, comprising:

(a) an anvil that includes a staple forming pocket, wherein the staple forming pocket extends along a longitudinal axis; and (b) a stapling assembly comprising:

(i) a deck surface, (ii) a first staple that includes a first crown extending along a first axis, and (iii) a second staple that includes a second crown and a first leg, wherein the second crown extends along a second axis, and (iv) a third staple that includes a third crown extending along a third axis, wherein the staple forming pocket of the anvil is configured to deform each of the first, second, and third staples to thereby transition the first, second, and third staples from a non-deformed state where the second staple extends along a first plane to a deformed state where the second staple extends along multiple planes including the first plane, wherein the first, second, and third staples form an overlapping staple pattern in response to being transitioned to the deformed state, wherein the first leg is disposed at a first angle relative to the second crown in the non-deformed state, wherein a portion of the first leg of the second staple and a portion of the first crown are positioned between the deck surface and the anvil, wherein the first axis is generally parallel to and offset from each of the second and third axes in the non-deformed state and in the deformed state, wherein the second axis is generally parallel to and offset from each of the first and third axes in the non-deformed state and in the deformed state, wherein the first, second, and third axes each extend substantially at a same angle relative to the longitudinal axis in the deformed state, wherein the first, second, and third staples form an interlocking shape in the deformed state, wherein first and second ends are deformed in opposite directions away from the longitudinal axis.

16. The surgical stapling instrument of claim 15, wherein the first leg of the second staple is configured to directly overlie the first crown to form the overlapping staple pattern between the first and second staples in response to the first and second staples being transitioned to the deformed state.

17. The surgical stapling instrument of claim 15, wherein the staple forming pocket of the anvil includes at least one sloped region configured to deform each of the first and second staples from the non-deformed state to the deformed state.

18. The surgical stapling instrument of claim 15, wherein the first leg terminates at a first end, wherein the second staple further comprises a second leg extending from the second crown and terminating at a second end, wherein the first and second ends of the second staple are separated by a first distance in the non-deformed state, wherein the first and second ends of the second staple are separated by a second distance in the deformed state, wherein the second distance is greater than the first distance.

19. The surgical stapling instrument of claim 15, wherein the first, second, and third staples form a linear overlapping staple pattern in response to being transitioned to the deformed state, wherein the linear overlapping staple pattern extends along a staple axis that is parallel to and offset from the longitudinal axis of the staple forming pocket in response to the first, second, and third staples being transitioned to the deformed state.

20. The surgical stapling instrument of claim 15, wherein the first, second, and third staples form an interlocking S shape in the deformed state.

* * * * *